United States Patent
Anderson et al.

(10) Patent No.: US 9,821,477 B2
(45) Date of Patent: Nov. 21, 2017

(54) STABILIZING APPARATUS FOR HIGHLY ARTICULATED PROBES WITH LINK ARRANGEMENT, METHODS OF FORMATION THEREOF, AND METHODS OF USE THEREOF

(71) Applicant: Medrobotics Corporation, Raynham, MA (US)

(72) Inventors: Robert Anderson, Norwell, MA (US); Gabriel Johnston, Raynham, MA (US); Ian J. Darisse, Brighton, MA (US); Joseph A. Stand, Holden, MA (US); Luis Bettencourt, Attleboro, MA (US); Todd Frangolis, North Easton, MA (US); Arnold E. Oyola, Northborough, MA (US); J. Christopher Flaherty, Aurburndale, FL (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 15/180,503

(22) Filed: Jun. 13, 2016

(65) Prior Publication Data

US 2017/0015007 A1    Jan. 19, 2017

Related U.S. Application Data

(63) Continuation of application No. 14/364,195, filed as application No. PCT/US2012/070924 on Dec. 20, 2012, now Pat. No. 9,364,955.

(Continued)

(51) Int. Cl.
*B25J 18/06* (2006.01)
*A61B 34/00* (2016.01)
(Continued)

(52) U.S. Cl.
CPC ............... *B25J 18/06* (2013.01); *A61B 34/30* (2016.02); *A61B 34/71* (2016.02); *B25J 9/065* (2013.01);
(Continued)

(58) Field of Classification Search
CPC .................. A61B 2019/2242; A61B 2034/301
See application file for complete search history.

(56) References Cited

U.S. PATENT DOCUMENTS 3,060,972 A    10/1962  Sheldon
3,557,780 A    1/1971   Sato
(Continued)

FOREIGN PATENT DOCUMENTS

EP          653922       11/2005
EP         1015068        9/2011
(Continued)

OTHER PUBLICATIONS

Chinese Office Action dated Dec. 7, 2016 issued in related application No. 201280070375.4.
(Continued)

*Primary Examiner* — Terence Boes
(74) *Attorney, Agent, or Firm* — Onello & Mello, LLP

(57) ABSTRACT

An apparatus for driving an articulating probe comprises an elongate probe constructed and arranged to articulate in at least one predetermined degree of motion and to transition from a flexible state to a rigid state, and a force transfer mechanism constructed and arranged to apply a force to the probe. The force is selected from the group consisting of a force that causes probe to articulate in the at least one predetermined degree of motion and a force that causes the probe to transition from the flexible state to the rigid state. The base structure is attached to portion of the force transfer mechanism and the elongate probe; the base structure com- (Continued)

prising one or more stabilizing elements constructed and arranged to resist undesired movement of the probe caused by force from the force transfer mechanism.

23 Claims, 23 Drawing Sheets

Related U.S. Application Data

(60) Provisional application No. 61/578,582, filed on Dec. 21, 2011, provisional application No. 61/681,340, filed on Aug. 9, 2012, provisional application No. 61/656,600, filed on Jun. 7, 2012.

(51) Int. Cl.
A61B 34/30 (2016.01)
B25J 9/06 (2006.01)

(52) U.S. Cl.
CPC ........ Y10S 901/21 (2013.01); Y10T 74/20323 (2015.01)

(56) References Cited

U.S. PATENT DOCUMENTS

| | | |
|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,643,653 A | 2/1972 | Takahashi et al. |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,479,914 A | 10/1984 | Baumrucker |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,180,276 A | 1/1993 | Hendrickson |
| 5,193,963 A | 3/1993 | McAffee et al. |
| 5,195,968 A | 3/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,347,993 A | 9/1994 | Tanaka |
| 5,386,741 A | 2/1995 | Rennex |
| 5,448,989 A | 9/1995 | Heckele |
| 5,524,180 A | 6/1996 | Wang et al. |
| 5,759,151 A | 6/1998 | Sturges |
| 5,815,640 A | 9/1998 | Wang et al. |
| 5,841,950 A | 11/1998 | Wang et al. |
| 5,907,664 A | 5/1999 | Wang et al. |
| 6,080,181 A | 6/2000 | Jensen et al. |
| 6,132,368 A | 10/2000 | Cooper |
| 6,223,100 B1 | 4/2001 | Green |
| 6,234,958 B1 | 5/2001 | Snoke et al. |
| 6,346,072 B1 | 2/2002 | Cooper |
| 6,440,061 B1 | 8/2002 | Wenner et al. |
| 6,743,239 B1 | 6/2004 | Kuehn et al. |
| 6,837,846 B2 | 1/2005 | Jaffe et al. |
| 6,837,847 B2 | 1/2005 | Ewers et al. |
| 6,916,306 B1 | 7/2005 | Jenkins et al. |
| 7,182,764 B2 | 2/2007 | Jenkins et al. |
| 7,357,774 B2 | 4/2008 | Cooper |
| 7,789,875 B2 | 9/2010 | Brock et al. |
| 7,819,885 B2 | 10/2010 | Cooper |
| 7,850,642 B2 | 12/2010 | Moll et al. |
| 7,854,109 B2 | 12/2010 | Zubiate et al. |
| 7,854,738 B2 | 12/2010 | Lee et al. |
| 7,867,241 B2 | 1/2011 | Brock et al. |
| 7,918,845 B2 | 4/2011 | Saadat et al. |
| 7,946,546 B2 | 5/2011 | Zubiate et al. |
| 7,972,298 B2 | 7/2011 | Wallace et al. |
| 8,075,476 B2 | 12/2011 | Vargas |
| 8,100,031 B2 | 1/2012 | Zubiate et al. |
| 8,192,422 B2 | 6/2012 | Zubiate et al. |

(56) References Cited

U.S. PATENT DOCUMENTS

| | | | |
|---|---|---|---|
| 8,394,054 | B2 | 3/2013 | Wallace et al. |
| 8,409,136 | B2 | 4/2013 | Wallace et al. |
| 8,459,138 | B2 | 6/2013 | Zubiate et al. |
| 8,974,408 | B2 | 3/2015 | Wallace et al. |
| 9,011,318 | B2 | 4/2015 | Choset et al. |
| 9,591,964 | B2 | 3/2017 | Choset et al. |
| 9,629,682 | B2 | 4/2017 | Wallace et al. |
| 2001/0013764 | A1 | 8/2001 | Blumenkranz et al. |
| 2002/0091374 | A1 | 7/2002 | Cooper |
| 2002/0133174 | A1 | 9/2002 | Charles et al. |
| 2002/0161281 | A1 | 10/2002 | Jaffe et al. |
| 2002/0188293 | A1 | 12/2002 | Manzo |
| 2003/0135203 | A1 | 7/2003 | Wang et al. |
| 2004/0138529 | A1 | 7/2004 | Wiltshire et al. |
| 2004/0193146 | A1 | 9/2004 | Lee et al. |
| 2005/0021050 | A1 | 1/2005 | Cooper |
| 2005/0033287 | A1 | 2/2005 | Sra |
| 2005/0065397 | A1 | 3/2005 | Saadat et al. |
| 2005/0090811 | A1 | 4/2005 | Doyle et al. |
| 2005/0113640 | A1 | 5/2005 | Saadat et al. |
| 2005/0215992 | A1 | 9/2005 | Jenkins et al. |
| 2005/0216033 | A1 | 9/2005 | Lee et al. |
| 2005/0222554 | A1 | 10/2005 | Wallace et al. |
| 2006/0052664 | A1 | 3/2006 | Julian et al. |
| 2007/0299387 | A1 | 12/2007 | Williams et al. |
| 2008/0027279 | A1 | 1/2008 | Abou El Kheir |
| 2008/0119868 | A1 | 5/2008 | Sharp et al. |
| 2008/0147091 | A1 | 6/2008 | Cooper |
| 2008/0163603 | A1 | 7/2008 | Zubiate et al. |
| 2008/0188869 | A1 | 8/2008 | Weitzner et al. |
| 2008/0245173 | A1 | 10/2008 | Schwerin et al. |
| 2009/0030428 | A1 | 1/2009 | Omori et al. |
| 2009/0171151 | A1 | 7/2009 | Choset et al. |
| 2009/0326556 | A1 | 12/2009 | Diolaiti et al. |
| 2010/0022825 | A1 | 1/2010 | Yoshie |
| 2010/0160735 | A1 | 6/2010 | Bakos |
| 2010/0160736 | A1 | 6/2010 | Padget et al. |
| 2010/0204713 | A1 | 8/2010 | Ruiz Morales |
| 2010/0224022 | A1 | 9/2010 | Choi et al. |
| 2010/0280325 | A1 | 11/2010 | Ibrahim et al. |
| 2011/0028790 | A1 | 2/2011 | Farr et al. |
| 2011/0028990 | A1 | 2/2011 | Cooper |
| 2011/0056320 | A1 | 3/2011 | Zubiate et al. |
| 2011/0066161 | A1 | 3/2011 | Cooper |
| 2011/0071543 | A1* | 3/2011 | Prisco ............... A61B 17/0218 606/130 |
| 2011/0105954 | A1 | 5/2011 | Cohen et al. |
| 2011/0152613 | A1 | 6/2011 | Zubiate et al. |
| 2011/0184241 | A1 | 7/2011 | Zubiate et al. |
| 2011/0213384 | A1 | 9/2011 | Jeong |
| 2011/0230896 | A1 | 9/2011 | Wallace et al. |
| 2011/0313243 | A1 | 12/2011 | Zubiate et al. |
| 2012/0004668 | A1 | 1/2012 | Wallace et al. |
| 2012/0209073 | A1 | 8/2012 | McWeeney et al. |
| 2013/0231679 | A1 | 9/2013 | Wallace et al. |
| 2015/0157412 | A1 | 6/2015 | Wallace et al. |
| 2015/0164491 | A1 | 6/2015 | Choset et al. |
| 2016/0174816 | A1 | 6/2016 | Choset et al. |
| 2017/0100197 | A1* | 4/2017 | Zubiate ............. A61B 17/3417 |
| 2017/0156569 | A1 | 6/2017 | Choset et al. |
| 2017/0215978 | A1 | 8/2017 | Wallace et al. |

FOREIGN PATENT DOCUMENTS

| | | |
|---|---|---|
| JP | 2007527296 | 9/2007 |
| JP | 2008504072 | 2/2008 |
| WO | 2010050771 | 5/2010 |
| WO | 2011024888 | 3/2011 |

OTHER PUBLICATIONS

Japanese Office Action dated Nov. 29, 2016 issued in corresponding Japanese Application No. 2014-548888, with English language translation.

Australian Examination Report dated Dec. 14, 2016 issued in corresponding Australian Application No. 2012358829.

European Office Action dated May 3, 2017 issued in corresponding European Application No. 12 860 859.3.

Reynolds, O., "On Efficiency of Belts or Straps as Communicators of Work", The Engineer, 1874, p. 396.

Swift, H. W., "Power Transmission by Belts: An Investigation of Fundamentals", The Institution of Mechanical Engineers, 1928.

Smith, G. A. et al., "Surgery", 1950, p. 817-821.

"Baby Robot", http://cyberneticzoo.com/wp-content/uploads/2010/03/Ticket-robot-russian-1973.pdf, 1970.

Rajac, "Variable-Pitch Transfer Mechanism", IBM Technical Disclosure Bulletin, 1974.

ZH Luo , "Theoretical and Experimental Study on Control of Flexible Robot Arms Using Direct Strain Feedback", 1992.

Bu Yonghong, Wang Yi, "The Identification of Geometric Link Parameters of Robot Manipulators", ACTA Automatica Sinica, 1992.

Zheng Nanning Wang Long Hu chao Liu Jiandin, "Improved BP Neural Net and Its Application to Handwritten Numeral Recognition", 1992.

Stefano Chiaverini, Bruno Siciliano, Olav Egeland, Robot Control in Singular Configurations—Analysis and Experimental Results, Experimental Robotics II, 1993, p. 25-34.

Antonio Bicchi, J. Kenneth Salisbury, David L. Brock, Experimental Evaluation of Friction Characteristics With an Articulated Robotic Hand, Experimental Robotics II, 1993, p. 153-167.

Claudio Melchiorri, Gabriele Vassura, Mechanical and Control Issues for Integration of an Arm-Hand Robotic System, Experimental Robotics II, 1993, p. 136-152.

Andrew K. Rist, Ellen Y. Lin, Bartholomew O. Nnaji, RALPH Application for Surface Mount Assembly, International Journal of Flexible Manufacturing Systems, 1993, p. 27-52.

R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.

Nobuyuki Furuya, Masatomo Matubara, An Algorithm of Motor Control by Software Servo System (2nd Report): Application to 4-Axes Scara Robot, Journal of the Japan Society of Precision Engineering , 1993, p. 423-428.

H.S. Moon, S.Y. Lee, S.J. Na, A Study on Selection of Gas Metal Arc Welding Parameters of Fillet Joints Using Neural Network, Journal of the Korean Welding Society, 1993, p. 151-160.

Byong Suk Kim, Computer-Assisted System for Accident Analysis and Mul-Function Protection in Industrial Robot, Papersearch.net (Korean Studies Information Co.), 1993, p. 61-64.

J. I. Arocena, R. W. Daniel, P. Elosegui, End Point Control of Compliant Robots, Experimental Robotics II, 1993, p. 435-449.

Ho Kyung Kim, Nonlinear Static Analysis and Determination of Initial Equilibrium States of Suspension Bridges, 1993, p. 177-186.

Gimdongha, imhyeongyo (Dong Ha Kim, Hyeon Kyo Lim) , Safe Speed Limit of Robot Arm During Teaching and Maintenance Work, 1993, p. 64-70.

Chang-Boo Kim, Seung-Hoon Lee, Inverse Dynamic Analysis of a Flexible Robot Arm With Multiple Joints by Using the Optimal Control Method, Journal of the Korean Society of Precision Engineering , 1993, p. 133-140.

Chang-Soo Han, The Optimum Design of a 6 D.O.F. Fully-Parallel Micromanipulator for Enhanced Robot Accuracy, Journal of the Korean Society of Precision Engineering , 1993, p. 42-51.

Nicholas Jackson, The Story Behind the Russian Robot Collie Patent Sketches, The Atlantic, 2011.

Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.

Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robot and CNC Machine System, Control R/D Team, Samsung Electronics, 1992, p. 1211-1214.

(56) References Cited

OTHER PUBLICATIONS

E.S. Jeon, S.H, Park, J.E. Oh, Singylarty Control Robot Wrist Joints Using Euler Parameters, Journal of the Korean Society of Precision Engineering , 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using Arma Prediction Model, 1992, p. 122-127.
Dae-Gab Gweon, Choong-Min Jung, Development of a Robot Wrist for the Assembly of Chamferless Parts, Journal of the Korean Society of Precision Engineering , 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries LTD, 1992, p. 233-238.
Jin-Geol Kim, A Study on the Robust Digital Tracking Control of a Robot With Flexible Joints, Journal of the Korean Society of Precision Control Engineering , 1992, p. 92-100.
Han-Sig Lee, The Prospects for the Future on Research of Flexible Automation and Robot System, 1992, p. 37-38.
Young Hood Joo, Seek Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot's Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering , 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joan Choi, Ki-Sang Hong, Hong Joeng, The Development of Intelligent Robot Using Vision and Speech Recognition System, Department of EE, Postech, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering , 1993, p. 170-177.
A Study on a Basic System Configuration for the PC Interface and the Robot Trajectory Generation, 1993, p. 354-358.
G.T. Yang, S.D. Ahn, S.C. Lee, Tip Position Control of Flexible Robot Arm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
ASEA Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
Expo-70 Robot—Vadim Matskevich's students, http://cyberneticzoo.com/wp-content/uploads/2010/03/Expo-70-MK-1969-02-p31-3.pdf, 1969.
Conductor Robot, http://cyberneticzoo.com/wp-content/uploads/2010/03/Ticket-robot-russian-1973.pdf, 1973.
Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.
Lee E. Weiss, Arthur C. Sanderson, Charles P. Neuman, "Dynamic Sensor Based Control of Robots with Visual Feedback", IEEE Journal of Robotics and Automation, 1987, p. 404-417.
Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.
Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.
Xu Hongbin, "Stability and performance robustness analysis of hybrid control for robot manipulators", Journal of UEST of China, vol. 22 No. 5, Oct. 1993, p. 501-505.
Francois Chaumette, Patrick Rives, Bernard Espiau, "Positioning of a Robot With Respect to an Object, Tracking It and Estimating Its Velocity by Visual Servoing", IEEE International Conf. on Robotics and Automation, 1991, p. 2248-2253.
A.V. Timofejev, N. V. Ivanova, "Expert System of the Control Programs Designing of Adaptive Robots", The Lenigrand Institute of Aircraft Instrumentation, 1991, p. 912-915.
W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.
Junji Furusho, Hiroshi Nagao, Naruse Makoto, "Multivariable Root Loci of Control Systems of Robot Manipulators with Flexible Driving Systems* : Distortion Feedback ", JSME International Journal, 1992, p. 65-73.
Potemkin, E., Astafurov, P., Osipov, A., Malenkov, M., Mishkinyuk, V., Sologub, P., "Remote-controlled robots for repair and recovery in the zones of high radiation levels ", Robotics and Automation, IEEE, 1992, p. 80-82.
S. L. Shishkin, "Adaptive control of a biped robot walking across a horizontal plane", International Journal of Adaptive Control and Signal Processing, 1992, p. 259-264.
Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.
Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.
J.D. Moon, D.W. Cho, "A component mode synthesis applied to mechanisms for an investigation of vibration", Journal of Sound and

(56) References Cited

OTHER PUBLICATIONS

Vibration; Department of Mechanical Engineering, Pohang Institute of Science and Technology, Pohang, Korea, 1992, p. 67-79.
Timopheev, A.V., Prokhorov, D.V., "Neural networks processing systems in recognition and control problems ", Neuroinformatics and Neurocomputers; IEEE, 1992, p. 820-828.
Jianguo Fu, Naresh K. Sinha, "An iterative learning scheme for motion control of robots using neural networks: A case study", Journal of Intelligent & Robotic Systems, 1993, p. 375-398.
Troccaz, J. Lavallee, S. Hellion, E., "A passive arm with dynamic constraints: a solution to safety problems in medical robotics", Systems Engineering in the Service of Humans', Conference Proceedings, 1993, p. 166-171.
Swarup, M. Gopal, "Comparative study on linearized robot models", Journal of Intelligent & Robotic Systems, 1993, p. 287-300.
H. Azaria, A. Dvir, "Algorithm optimization using a rule-based system. A case study: The Direct Kinematic Solution in robotics", Journal of Intelligent & Robotic Systems, 1993, p. 309-324.
Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.
K. Periyasamy, V. S. Alagar, T. D. Bui, "A formal framework for design and verification of robotic agents", Journal of Intelligent & Robotic Systems, 1993, p. 173-200.
S. Nicosia, A. Tornambè, P. Valigi, "State estimation in robotic manipulators: Some experimental results", Journal of Intelligent & Robotic Systems,, 1993, p. 321-351.
Dimitrios M. Emiris, Vassilios D. Tourassis, "Singularity-robust decoupled control of dual-elbow manipulators", Journal of Intelligent & Robotic Systems, 1993, p. 225-243.
M.M. Bayoumi, "Adaptive Control of Robots with Rigid Links: A Status Report", Department of Electrical Engineering, Queen's University Ontario, Canada (IEEE), 1993, p. 232-236.
Y. Edan, B. A. Engel, G. E. Miles, "Intelligent control system simulation of an agricultural robot", Journal of Intelligent & Robotic Systems, 1993, p. 267-284.
Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.
Yalou Huang; Guizhang Lu, "Force Analysis and Hybrid Control Scheme for Multiple Robot Manipulators", Artificial Intelligence and Robotics Research Laboratories; Dept. of Computer and System Sciences; Nankai University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.
E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.
A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.
E. V. Panteley, A. A. Stotsky, "Adaptive trajectory/force control scheme for constrained robot manipulators", International Journal of Adaptive Control and Signal Processing, 1993, p. 489-496.
Filaretov, V.F., "A Synthesis of Adaptive Control Systems for Industrial Robots ", Electronic Mfg Technology Symposium, 1993, p. 168-171.

S. Zenkevich, A. Maximov, A. Nazarova, A. Korshunov, "Control of robot-based assembly cell", Lecture Notes in Control and Information Sciences , 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots; an adaptive image-based approach, Technical Report", Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol. 1984, p. 222-230.
Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with a Hand-eye Coordinated Camera", IEEE Transactions on Systems, man, and Cybernetics, 1990, p. 1172-1183.

(56) References Cited

OTHER PUBLICATIONS

Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables—snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cyberrnetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME Angular international journal, 1992, p. 406-412.
Ph, Cinquin, et. al, IGOR: Image Guided Operating Robot, Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a Hybrid Virtual-Real Structure, RoManSy 9: Proceedings of the Ninth CISM-IFToMM Symposium on Theory and Practice of Robots and Manipulators.

James K. Mills, Hybrid Actuator for Robot Manipulators: Design, Control, and Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N. A., Faure A., Klepatch A.A., Podladchikova L.N., Rybak I.A. , Model of Foveal Visual Preprocessor, Intelligent Robots and Computer Active Vision XIV: Algorithms, Techniques, Active Vision, and Materials Handling, 1995, p. 588-596.
International Search Report and Written Opinion dated Apr. 6, 2012 issued in related International Application No. PCT/US2011/044811.
International Search Report and Written Opinion dated May 30, 2012, issued in related International Application No. PCT/US2011/057282.
International Search Report and Written Opinion dated May 31, 2012, issued in related International Application No. PCT/US2011/060214.
International Search Report and Written Opinion dated Nov. 28, 2012, issued in related International Application No. PCT/US2012/040414.
International Search Report and Written Opinion dated Feb. 27, 2013, issued in related International Application No. PCT/US2012/054802.
International Search Report and Written Opinion dated Apr. 25, 2013, issued in related International Application No. PCT/US2012/070924.
International Search Report and Written Opinion dated Dec. 9, 2013, issued in related International Application No. PCT/US2013/054326.
International Search Report and Written Opinion dated May 19, 2014, issued in related International Application No. PCT/US2014/010808.
Australia Office Action dated Jun. 19, 2014, issued in related Australia Application No. 2011283048.
Extended European Search Report dated Sep. 16, 2014 issued in European Application No. 12793169.9-1660 / 2713931.
Extended European Search Report dated Jul. 9, 2015 in related European Application No. 12860859.3.
"Stabilizing Apparatus for Highly Articulated Probes With Link Arrangement, Methods of Formation Thereof, and Methods of Use Thereof", Specification, Drawings, Claims and Prosecution History, of U.S. Appl. No. 14/364,195, filed Jun. 10, 2014, by Arnold Oyola, et al.
Corresponding OA dated Aug. 16, 2016, issued in related European Application No. 12860859.3-1666.
Chinese Office Action dated Aug. 15, 2017 issued in corresponding Chinese Application No. 201280070375.4 with English language summary.

(56) References Cited

OTHER PUBLICATIONS

Japanese Office Action dated Aug. 15, 2017 issued in corresponding Japanese Application No. 2014-548888, with English language machine translation.

* cited by examiner

STABILIZING APPARATUS FOR HIGHLY ARTICULATED PROBES WITH LINK ARRANGEMENT, METHODS OF FORMATION THEREOF, AND METHODS OF USE THEREOF

RELATED APPLICATIONS

This application is a continuation application of U.S. Ser. No. 14/364,195 filed Jun. 10, 2014, which claims the benefit under 35 U.S.C. 371 to PCT/US2012/070924, filed Dec. 20, 2012, which claims the benefit of U.S. Provisional Application No. 61/578,582, filed Dec. 21, 2011, the content of which is incorporated herein by reference in its entirety.

This application claims the benefit of U.S. Provisional Application No. 61/681,340, filed Aug. 9, 2012, the content of which is incorporated herein by reference in its entirety.

This application claims the benefit of U.S. Provisional Application No. 61/656,600, filed Jun. 7, 2012, the content of which is incorporated herein by reference in its entirety.

This application is related to PCT Application No PCT/US2011/060214, filed Nov. 10, 2011, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2012/054802, filed Sep. 12, 2012, the content of which is incorporated herein by reference in its entirety.

This application is related to U.S. Provisional Application No. 61/534,032, filed Sep. 13, 2011, the content of which is incorporated herein by reference in its entirety.

This application is related to PCT Application No PCT/US2012/032279, filed Apr. 5, 2012, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No PCT/US2012/040414, filed Jun. 1, 2012, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No PCT/US2011/057282, filed Oct. 21, 2011, the content of which is incorporated herein by reference in its entirety.

This application is related to PCT Application No PCT/US2011/044811, filed Jul. 21, 2011, the content of which is incorporated herein by reference in its entirety.

This application is related to U.S. Provisional Application No. 61/368,257, filed Jul. 28, 2010, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

Embodiments of the present inventive concepts relate generally to the field of robotics and, more particularly, to three-dimensional, flexible, steerable robotic devices, and methods of forming and controlling the same.

BACKGROUND

As less-invasive medical techniques and procedures become more widespread, medical professionals, such as surgeons, may employ snake-like robotic systems having highly articulated multi-link probes to access parts of the human anatomy that were otherwise difficult to reach. With the use of such robotic systems, medical professionals may be able to replace open-cavity surgical procedures with less invasive procedures.

Such articulating probes can be subject to significant forces in order to control or lock the linking mechanism, and subject the probe to undesired movements and adversely affect the performance of the articulating probe.

SUMMARY

Embodiments of the present inventive concepts may be directed to articulating robotic systems, robotic system user interfaces, human interface devices for controlling robotic systems and methods of controlling robotic systems.

In an aspect of inventive concepts, an apparatus for driving an articulating probe is provided, the apparatus including at least one elongate probe constructed and arranged to articulate in at least one predetermined degree of motion and to transition from a flexible state to a rigid state, a force transfer mechanism constructed and arranged to apply a force to the at least one elongate probe. The force is selected from the group consisting of a force that causes the at least one elongate probe to articulate in the at least one predetermined degree of motion and a force that causes the at least one elongate probe to transition from the flexible state to the rigid state. The base structure is attached to at least a portion of the force transfer mechanism and the at least one elongate probe; the base structure including one or more stabilizing elements constructed and arranged to resist undesired movement of the at least one elongate probe caused by force from the force transfer mechanism.

In an embodiment, the at least one of the stabilizing elements is constructed and arranged to resist twisting of the base structure.

In an embodiment, the at least one of the stabilizing elements is constructed and arranged to resist flexing of the base structure.

In an embodiment, the at least one of the stabilizing elements is constructed and arranged to resist compression of the base structure.

In an embodiment, the at least one of the stabilizing elements is constructed and arranged to resist stretching of the base structure.

In an embodiment, at least one of the stabilizing elements is constructed and arranged to resist lengthening of the base structure.

In an embodiment, the base structure includes a housing and wherein at least one of the stabilizing elements includes a rib connected to the housing.

In an embodiment, the base structure includes a housing including a first portion and a thicker second portion and wherein the stabilizing element includes the thicker second portion.

In an embodiment, the one or more stabilizing elements includes a force distribution plate.

In an embodiment, the base structure includes a plastic housing and wherein the force distribution plate is a metal plate attached to the plastic housing.

In an embodiment, the force transfer mechanism includes at least one cable and at least one bobbin, wherein applying a force to the at least one elongate probe includes rotating the at least one bobbin, and wherein the at least one bobbin is attached to and stabilized by the force distribution plate.

In an embodiment, the force transfer mechanism further includes at least two cables and at least two corresponding bobbins, wherein applying a force to the at least one elongate probe further includes rotating the at least two bobbins, and wherein the at least two bobbins are attached to the force distribution plate.

In an embodiment, the force transfer mechanism further includes at least three cables and at least three bobbins, wherein applying a force to the at least one elongate probe further includes rotating the at least three bobbins, and wherein the at least three bobbins is attached to the force distribution plate.

In an embodiment, the force transfer mechanism includes at least one cable, at least one bobbin and at least one cart, wherein applying a force to the at least one elongate probe includes rotating the at least one bobbin, wherein the at least one cart is constructed and arranged to advance and retract the at least one elongate probe, and wherein the at least one bobbin and the at least one cart are attached to the force distribution plate.

In an embodiment, the force transfer mechanism includes at least one gear, wherein advancing or retracting the at least one elongate probe includes rotating the at least one gear.

In an embodiment, the at least one gear includes at least one lead screw for driving an at least one cart, wherein the at least one cart is movably mounted on the at least one lead screw.

In an embodiment, the base structure includes a first portion operably attachable to a second portion, and wherein the at least one stabilizing element includes at least one projection extending from the first portion and at least one recess positioned in the second portion to receive the at least one projection.

In an embodiment, the at least one projection includes a tongue plate and the at least one recess includes a slot for receiving the tongue plate.

In an embodiment, the base structure includes a first portion, a second portion, and the at least one stabilizing element includes a latching assembly for operably attaching the first portion to the second portion. In an embodiment, the latching assembly is spring-loaded.

In an embodiment, the apparatus further includes at least one cart attached to the at least one elongate probe, wherein the at least one cart includes a first cart that is constructed and arranged to advance and retract the elongate probe, and wherein the at least one stabilizing element includes an elongate guide fixture constructed and arranged to slidingly guide the first cart. In an embodiment, the apparatus further includes a second elongate probe and a second cart attached to the second elongate probe, wherein the second cart is constructed and arranged to advance and retract the second elongate probe, and wherein the stabilizing element further includes a second guide fixture constructed and arranged to slidingly guide the second cart.

In an embodiment, the second guide fixture is a rail. In an embodiment, the second guide fixture is a solid cylindrical metal rail. In an embodiment, the second guide fixture includes an elongate slot that receives and communicates with an at least one of a corresponding male fixture of at least one of the first and the second carts.

In an embodiment, the force that causes the at least one elongate probe to transition from the flexible state to the rigid state includes a force of at least 1 pound.

In an embodiment, the force that causes the at least one elongate probe to transition from the flexible state to the rigid state includes a force of at least 10 pounds.

In an embodiment, the force that causes the at least one elongate probe to transition from the flexible state to the rigid state includes a force of at least 20 pounds.

In an embodiment, the force that causes the at least one elongate probe to transition from the flexible state to the rigid state includes a force of approximately 30 pounds.

In an embodiment, the force transfer mechanism includes at least one cable constructed and arranged to transmit a force that causes the at least one elongate probe to transition from the flexible state to the rigid state.

In an embodiment, the force transfer mechanism includes at least two cables constructed and arranged to collectively transmit a force that causes the at least one elongate probe to transition from the flexible state to the rigid state.

In an embodiment, the at least two cables are further constructed and arranged to transmit the articulating force to articulate the at least one elongate probe.

In an embodiment, the force transfer mechanism includes at least three cables constructed and arranged to collectively transmit a force that causes the at least one elongate probe to transition from the flexible state to the rigid state. In an embodiment, the at least three cables are further constructed and arranged to transmit the articulating force to articulate the at least one elongate probe.

In an embodiment, the at least one elongate probe includes a first probe arm and a second probe arm, the first probe arm enclosing the second probe arm, wherein the articulation mechanism is constructed and arranged to drive the first and second probe arms longitudinally with respect to each other and wherein the force transfer mechanism includes a locking mechanism to independently lock or release each of the first and second probe arms in states of flexibility and rigidity in the flexible state or the rigid state.

In an embodiment, the at least one elongate probe includes a steerable distal end. In an embodiment, the at least one predetermined degree of motion includes three degrees of motion about which the steerable distal end can be steered.

In an embodiment, the base structure includes a feeding structure through which the at least one elongate probe is fed from the base structure.

In an embodiment, the feeding structure includes at least one slidable actuating carriage constructed and arranged to advance and retract the at least one elongate probe.

In an embodiment, the one or more stabilizing elements include at least two rails on which the at least one slidable actuating carriage slides, the at least two rails constructed and arranged to substantially prevent movement of the at least one slideable actuating carriage and cables in directions other than predetermined motion along the longitudinal axis of the at least two rails.

In an embodiment, the at least two rails includes two spaced apart and parallel rails constructed and arranged to substantially prevent twisting or bending of the base structure. In an embodiment, the at least two rails are solid. In an embodiment, the at least two rails are hollow.

In an embodiment, the at least one slideable actuating carriage includes first and second slidable actuating carriages to respectively advance first and second probe arms of the articulating probe, the second probe arm slidable within the first probe arm.

In an embodiment, the first probe includes a plurality of inner links and the second probe includes a plurality of outer links, wherein the inner and outer links articulate with respect to each other.

In an embodiment, the feeding structure includes at least one elongate lead screw arranged to be rotated so as to drive actuation of the at least one slidable actuating carriage.

In an embodiment, the at least one elongate lead screw includes two parallel and spaced apart lead screws arranged to substantially prevent twisting or bending of the base structure.

In an embodiment, the stabilizing elements include at least one metal mounting plate to which the at least one elongate lead screw is mounted so as to minimize non-linear movement of the slidable carriages with respect to the feeding structure.

In an embodiment, the at least one slidable actuating carriage includes Teflon-coated bushings arranged to substantially prevent movement of the actuating carriage in directions other than predetermined motion along the longitudinal axis of the at least one elongate lead screws.

In an embodiment, the force transfer mechanism includes at least one gear connecting the feeding structure to drive the articulating probe and wherein the stabilizing elements include helical threads on the at least one gear to increase the connective area between the base structure and the feeding structure.

In an embodiment, the force transfer mechanism includes at least two cables housed within the feeding structure and arranged to steer a distal end of the at least one elongate probe.

In an embodiment, the at least two cables includes three cables arranged to steer a distal end of the at least one elongate probe in three degrees of freedom.

In an embodiment, the at least two cables are arranged to drive the locking mechanism.

In an embodiment, all of the force transfer mechanism located within the feeding structure includes a sub-assembly constructed independently from the feeding structure.

In an embodiment, the feeding structure is secured to the sub-assembly so as to increase the rigidity of the sub-assembly during articulation of the at least one elongate probe.

In an embodiment, the force transfer mechanism includes at least one rotatable bobbin housed within the feeding structure to drive articulation of the at least one probe arm.

In an embodiment, the at least one rotatable bobbin drives articulation of the at least two cables.

In an embodiment, the bobbins are mounted to a mounting plate, the mounting plate further mounted to the sub-assembly.

In an embodiment, the sub-assembly further includes the at least one slidable actuating carriage, the at least two rails, and the at least one elongate lead screw.

In an embodiment, the feeding structure is a detachable portion of the base structure, wherein an interface between the feeding structure and non-detachable portion of the base structure includes at least one alignment feature that aligns the feeding structure with the base structure.

In an embodiment, the alignment features include at least one protrusion of the interface to fixedly engage with at least one alignment slot of the interface.

In an embodiment, the at least one alignment feature includes at least two slots of the interface to interface with at least two alignment pegs of the interface.

In an embodiment, the at least one protrusion includes a vertically oriented alignment plate.

In an embodiment, the vertically oriented alignment plate extends across at least one half of a width of the feeding structure.

In an embodiment, the at least one alignment feature includes two or more ball plungers arranged to engage with the vertically oriented alignment plate so as to further align the vertically oriented alignment plate within an at least one alignment slot and reduce motion of the alignment plate within the at least one alignment slot.

In an embodiment, the two or more ball plungers are arranged to prevent improper orientation of the alignment plate within the at least one alignment slot.

In an embodiment, the alignment plate includes an alignment rib on a face of the alignment plate so as to reduce sliding of the alignment plate across the length of the alignment slot.

In an embodiment, the alignment plate includes a tongue slot at the proximal end of the alignment plate, the tongue slot arranged to engage and interlock with an articulating tongue when the articulating tongue engages with the tongue slot, the articulating tongue attached to the non-detachable portion of the base structure.

In an embodiment, the interface includes at least two protrusions and two slots arranged to interface with each other upon connecting the feeding structure with the non-detachable portion of the base structure, wherein a first protrusion and a second protrusion are horizontally separated from each other by at least a half of the horizontal maximum length of the support structure in order to substantially align the base unit and support structure and prevent a rotating yaw of the support structure.

In an embodiment, the interface includes at least two protrusions and two slots arranged to interface with each other upon connecting the feeding structure to the base structure, wherein the first and second protrusions are located directly about two sides of a first electrical connector in the interface, the first and second protrusions arranged to mate with first and second slots in the interface, the first electrical connector arranged to mate with a second electrical connector located in the interface.

In an embodiment, the first and second protrusions are tapered to provide fine alignment of the first and second electrical connectors with each other.

In an embodiment, the interface includes one or more horizontally oriented spring-loaded slots and one or more corresponding horizontally oriented pins arranged to engage the spring-loaded slots upon connecting the feeding structure to the base structure.

In an embodiment, a portion of the force transfer mechanism secured within the base structure is driven by at least one force-generating unit.

In an embodiment, the at least one force generating unit includes a motor. In an embodiment, the motor generates force through at least one of a solenoid, valve, cylinder, hydraulic, and pneumatic.

In an embodiment, the at least one force-generating unit is housed outside of the detachable feeding structure.

In an embodiment, the base structure includes a base plate, the base plate including a stand connecting interface for mounting the base structure to a stand structure, wherein the stand connecting interface is integrated within the base plate of the base structure.

In an embodiment, the stand connecting interface is electrically isolated from the rest of the base unit.

In an embodiment, the stand connecting interface includes at least one of plastic spacers, a key hole slotted plastic isolation plate, and insulated standoffs in order to electrically isolate the stand interface from the rest of the base unit.

In an embodiment, the at least one or more stabilizing elements includes one or more vertically oriented posts extending between the ground connecting interface and a chassis of the base structure.

In an embodiment, the vertically oriented posts are constructed of solid metal.

In an embodiment, the vertically oriented posts extend from a plate in the chassis.

In an embodiment, the base structure includes a Faraday cage connecting a chassis of the base structure so as to prevent undesired electrical interference from external sources and emission to other electrical devices.

In an embodiment, the apparatus includes an introducer conduit attached to the base structure, the introducer conduit arranged to guide the at least one probe arm along a predetermined path.

In an embodiment, the introducer conduit is fastened to a bearing block securing the at least one lead screw so as to align the introducer conduit with the at least one slidable carriage.

In an embodiment, the at least one force translating unit is arranged to translate at least about thirty pounds of force while the at least one or more stabilizing elements substantially limits motion of the at least one probe arm to the driven at least one predetermined degree of motion.

In an aspect of inventive concepts, the apparatus includes at least one elongate probe arm constructed and arranged to articulate in at least one predetermined degree of motion, an articulation mechanism constructed and arranged to drive the articulation of the at least one probe arm in the at least one predetermined degree of motion, a base structure arranged to remain stationary with respect to the articulation mechanism of the at least one elongate probe arm and to fixedly secure at least a portion of the articulation mechanism, the base structure including a support structure extending the articulation mechanism from the base structure to the at least one elongate probe arm, the support structure arranged to substantially limit motion of the at least one probe arm to the driven at least one predetermined degree of motion, wherein the at least one probe arm includes a first probe arm and a second probe arm, the first probe arm enclosing the second probe arm, wherein the articulation mechanism is constructed and arranged to drive the first and second probe arms longitudinally with respect to each other, and wherein the articulation mechanism includes a locking mechanism to independently lock or release each of the first and second probe arms in states of rigidity and flexibility, respectively.

In an embodiment, the probe arm includes a steerable distal end.

In an embodiment, the at least one degree of motion includes three degrees of motion about which the steerable distal end can be steered.

In an embodiment, the at least one probe arm includes a proximate end and wherein the base structure includes a feeding conduit through which the at least one probe arm is fed from the base structure.

In an embodiment, the feeding conduit includes at least one slidable actuating carriage arranged within the feeding conduit to advance and retract the at least one probe arm.

In an embodiment, the at least one actuating carriage includes first and second slidable actuating carriages to advance first and second probe arms of the at least one probe arm, the second probe arm slidable within the first probe arm.

In an embodiment, the feeding conduit includes at least two rails on which the at least one slidable actuating carriage slides, the at least two rails constructed and arranged to substantially prevent movement of the actuating carriage and cables in directions other than predetermined motion along the longitudinal axis of the rails.

In an embodiment, the at least two rails are parallel and spaced apart so as to substantially prevent twisting or bending of the base unit.

In an embodiment, the rails include slots arranged to guide sliding of the slidable carriages.

In an embodiment, the rails are cylindrical.

In an embodiment, the feeding conduit includes at least one elongate lead screw arranged to be rotated so as to drive actuation of the at least one slidable actuating carriage.

In an embodiment, the at least one elongate lead screws includes two lead screws.

In an embodiment, the at least one elongate lead screws is mounted to the feeding conduit with at least one metal plate so as to minimize non-linear movement of the slidable carriages with respect to the feeding conduit.

In an embodiment, the slidable actuating carriages include Teflon-coated bushings arranged to engage the at least one elongate lead screws.

In an embodiment, the at least one lead screws is supported by at least one bearing having a bearing block affixed to the feeding conduit so as to substantially prevent movement of the at least one elongated lead screw other than the rotation for driving actuation of the at least on slidable actuation carriage.

In an embodiment, the at least one bearing is a thrust bearing.

In an embodiment, the at least one elongated lead screw is supported by at least one spherical bearing so as to self align the lead screw with a bearing block securing the lead screw and substantially preventing movement of the at least one elongated lead screw other than the rotation for driving actuation of the at least on slidable actuation carriage.

In an embodiment, the at least one spherical bearing is located at the distal end of the lead screw and the thrust bearing is located at the proximal end of the lead screw.

In an embodiment, the articulation mechanism includes at least one helical gear to drive the articulation mechanism and to increase the connective area between the support structure and the portion of the articulation mechanism fixedly secured to the base unit.

In an embodiment, the at least one helical gear drives actuation of the at least one elongate lead screw.

In an embodiment, the articulation mechanism includes at least two cables housed within the feeding conduit and arranged to articulate the at least one probe arm.

In an embodiment, the articulation mechanism includes at least two cables housed within the feeding conduit and arranged to steer a distal end of the at least one probe arm.

In an embodiment, the at least two cables includes three cables arranged to steer a distal end of the at least one probe arm in three degrees of motion.

In an embodiment, the at least two cables are arranged to drive the locking mechanism.

In an embodiment, a portion of the articulation mechanism not secured within the base unit includes a sub-assembly constructed independently from the feeding conduit.

In an embodiment, the feeding conduit is secured to the sub-assembly so as to increase the rigidity of the sub-assembly during articulation.

In an embodiment, the articulation mechanism includes at least one rotatable bobbin housed within the feeding unit to drive articulation of the at least one probe arm.

In an embodiment, the at least one rotatable bobbin drives articulation of the at least two cables.

In an embodiment, the bobbins are mounted to a mounting plate, the mounting plate further mounted to the sub-assembly.

In an embodiment, the sub-assembly further includes the at least one slidable actuating carriage, the at least two rails, and the at least one elongate lead screw.

In an embodiment, the mounting plate includes alignment features that align the mounting plate with the base unit.

In an embodiment, the alignment features includes at least one slot constructed to fixedly engage with at least one protrusion of the base unit.

In an embodiment, the at least one protrusion of the base unit includes two or more alignment pegs.

In an embodiment, the alignment features include at least one protrusion constructed to fixedly engage with at least one slot of the base unit.

In an embodiment, the at least one protrusion includes an alignment plate substantially orthogonal to the mounting plate.

In an embodiment, the alignment plate extends across at least one half of a width of the mounting plate.

In an embodiment, the at least one alignment slot includes ball plungers arranged to engage with the alignment plate so as to further align the alignment plate within the at least one alignment slot and reduce motion of the alignment plate within the at least one alignment slot.

In an embodiment, the ball plungers are arranged to prevent improper orientation of the alignment plate within the at least one alignment slot.

In an embodiment, the alignment plate includes an alignment rib on a face of the alignment plate so as to reduce sliding of the alignment plate across the length of the alignment slot.

In an embodiment, the alignment plate includes a tongue slot at the proximal end of the alignment plate, the tongue slot arranged to engage and interlock with an articulating tongue when the articulating tongue engages with the tongue slot, the articulating tongue attached to the base unit so as to substantially prevent a rotating pitch of the support structure.

In an embodiment, the portion of the articulation mechanism includes at least one force-generating unit and wherein the support structure includes at least one force translating unit driven by the at least one force-generating unit.

In an embodiment, the at least one force generating unit includes a motor.

In an embodiment, the motor generates force through at least one of a solenoid, valve, cylinder, hydraulic, and pneumatic.

In an embodiment, the at least one force translating unit is arranged to translate at least about thirty pounds of force while the support structure substantially limits motion of the at least one probe arm to the driven at least one predetermined degree of motion.

In an embodiment, the base structure includes a feeding structure separable from the base structure and a mounting interface for connecting the base structure and feeding structure together.

In an embodiment, the mounting interface includes at least two protrusions and two slots arranged to interface with each other upon connecting the base structure with the feeding structure, wherein a first protrusion and a second protrusion are horizontally separated from each other by at least a half of the horizontal maximum length of the feeding in order to substantially align the base structure and feeding structure and prevent a rotating yaw of the base structure.

In an embodiment, the first and second protrusions are located about two sides of a first electrical connector in the mounting interface, the first and second protrusions arranged to mate with first and second slots in the mounting interface, the first electrical connector arranged to mate with a second electrical connector located in the mounting interface.

In an embodiment, the first and second protrusions are tapered to provide fine alignment of the first and second electrical connectors with each other.

In an embodiment, the mounting interface includes one or more horizontally oriented spring-loaded slots and one or more corresponding horizontally oriented pins arranged to engage the spring-loaded slots upon connecting the base structure with the feeding structure.

In an embodiment, the base structure includes a ground connecting interface for mounting the base structure to a ground-fixed structure.

In an embodiment, the ground connecting interface is integrated within a plate of the base unit. In an embodiment, the ground connecting interface is electrically isolated from the rest of the base unit.

In an embodiment, the ground connecting interface includes at least one of plastic spacers, a key hole slotted plastic isolation plate, and insulated standoffs in order to electrically isolate the stand interface from the rest of the base unit. In an embodiment, the support structure includes one or more vertically oriented beams extending between the ground connecting interface and a chassis of the base structure. In an embodiment, the vertically oriented beams are constructed of solid metal.

In an embodiment, the vertically oriented beams extend from a plate.

In an embodiment, the base structure includes a Faraday cage connecting a chassis of the base structure with the ground connecting interface so as to prevent undesired electrical interference from external sources and emission to other electrical devices.

In an embodiment, the apparatus further including an introducer conduit attached to the base structure, the introducer conduit arranged to guide the at least one probe arm along a predetermined path. In an embodiment, the introducer conduit is fastened to the at least one metal plate the at least one lead screw so as to align the introducer conduit with the at least one slidable carriage.

In an aspect of inventive concepts, a method includes providing at least one elongate probe constructed and arranged to articulate in at least one predetermined degree of motion and to transition from a flexible state to a rigid state, providing a force transfer mechanism constructed and arranged to apply a force to the at least one elongate probe, said force selected from the group consisting of a force constructed and arranged to cause the at least one elongate probe to articulate in the at least one predetermined degree of motion and a force constructed and arranged to cause the at least one elongate probe to transition from the flexible state to the rigid state. The method further includes providing a base structure attached to at least a portion of the force transfer mechanism and the at least one elongate probe, the base structure including one or more stabilizing elements constructed and arranged to resist undesired movement of the elongate probe caused by force from the force transfer mechanism. The method further includes articulating the at least one elongate probe with the force transfer mechanism by placing a first probe of the at least one elongate probe in a flexible state, articulating the first probe in a predetermined direction, placing the first probe in a state of rigidity, placing a second probe of the at least one elongate probe in a flexible state, and advancing the second probe in the predetermined direction relative to the first probe.

BRIEF DESCRIPTION OF THE DRAWINGS

The foregoing and other objects, features and advantages of embodiments of the present inventive concepts will be apparent from the more particular description of embodiments, as illustrated in the accompanying drawings in which like reference characters refer to the same elements throughout the different views. The drawings are not necessarily to scale, emphasis instead being placed upon illustrating the principles of the embodiments.

DETAILED DESCRIPTION OF EMBODIMENTS

Figure 1A:
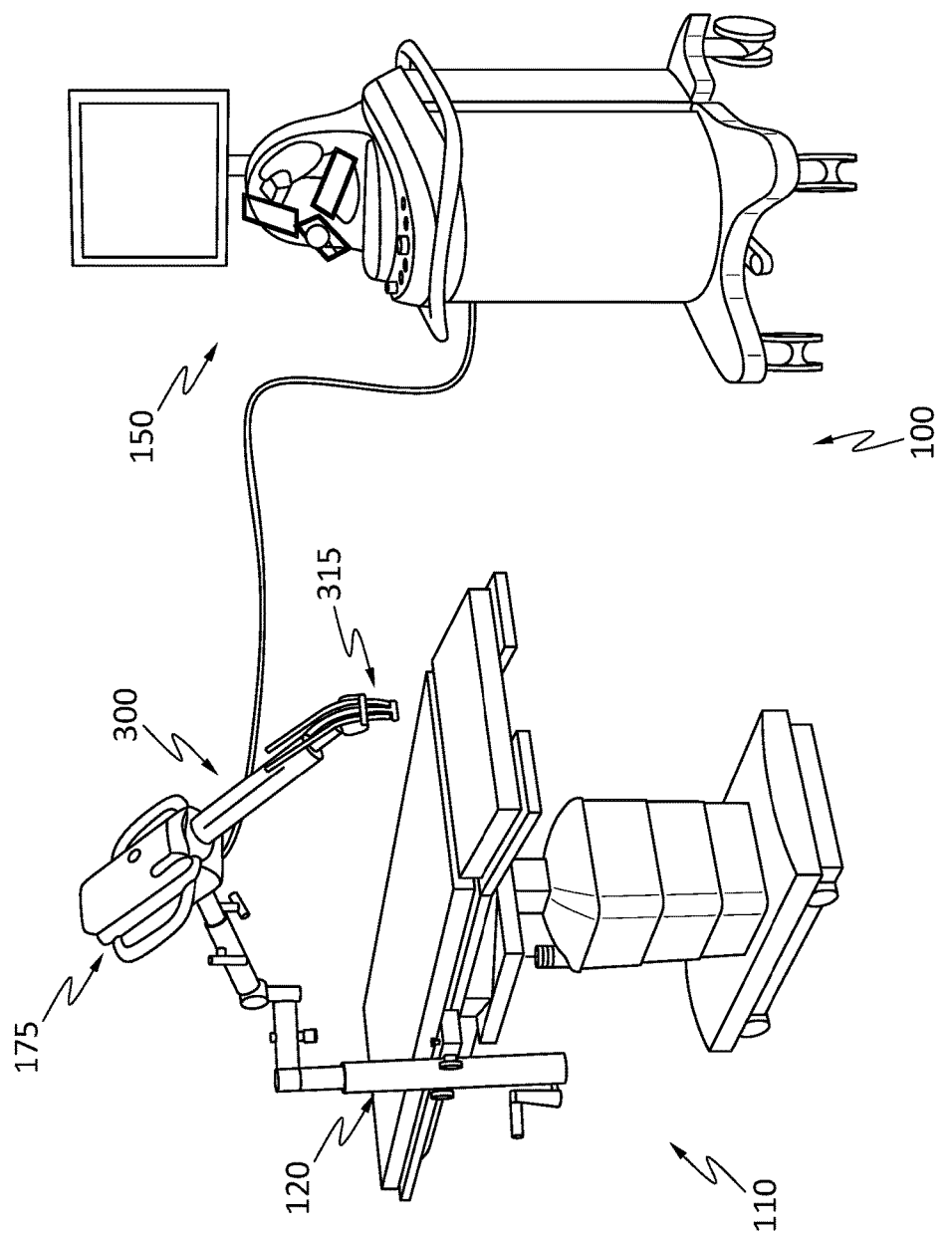
FIG. 1A is a perspective illustrative view of an articulating probe system according to an embodiment of inventive concepts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap. There are numerous types of steerable multi-linked, highly articulated probes. Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath. Howard Choset's U.S. patent application Ser. No. 11/630,279, which is hereby incorporated by reference in its entirety, discloses a feeder mechanism for advancing and retracting both an inner core and an outer sleeve, as well as selectively applying tension to control cables used for steering and causing either the inner core or outer sleeve to transition between a rigid state and a limp state.

Figure 11B:
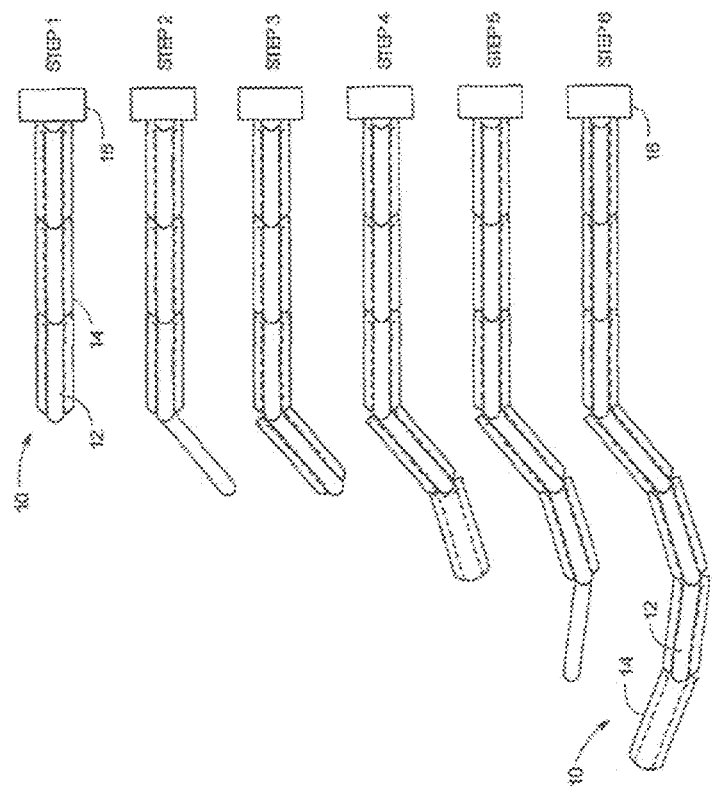
FIGS. 11A-11C are graphic demonstrations of a highly articulated probe device, according to embodiments of the present inventive concepts.
Figure 11A:
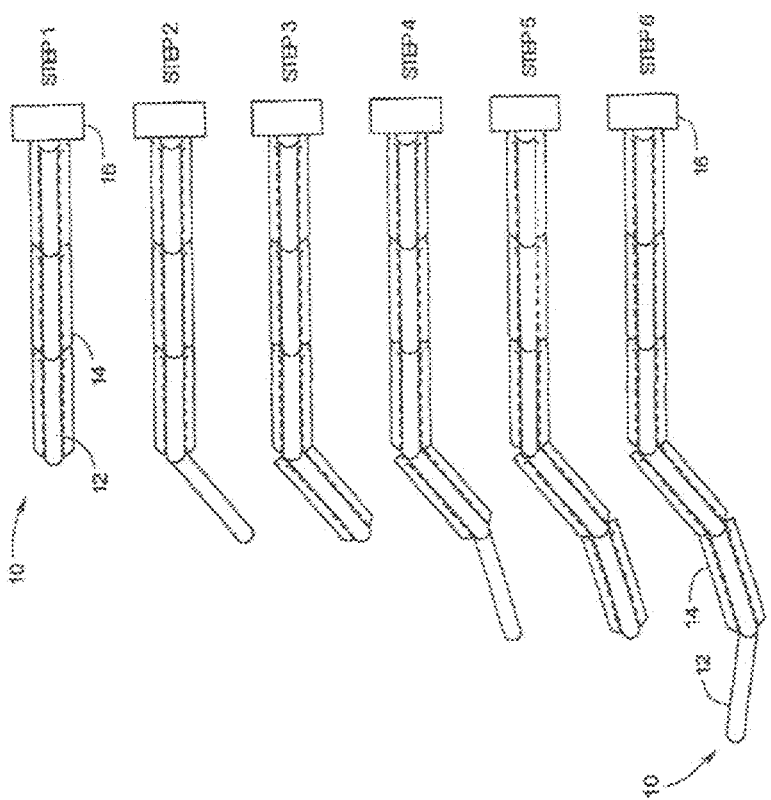
Figure 11C:
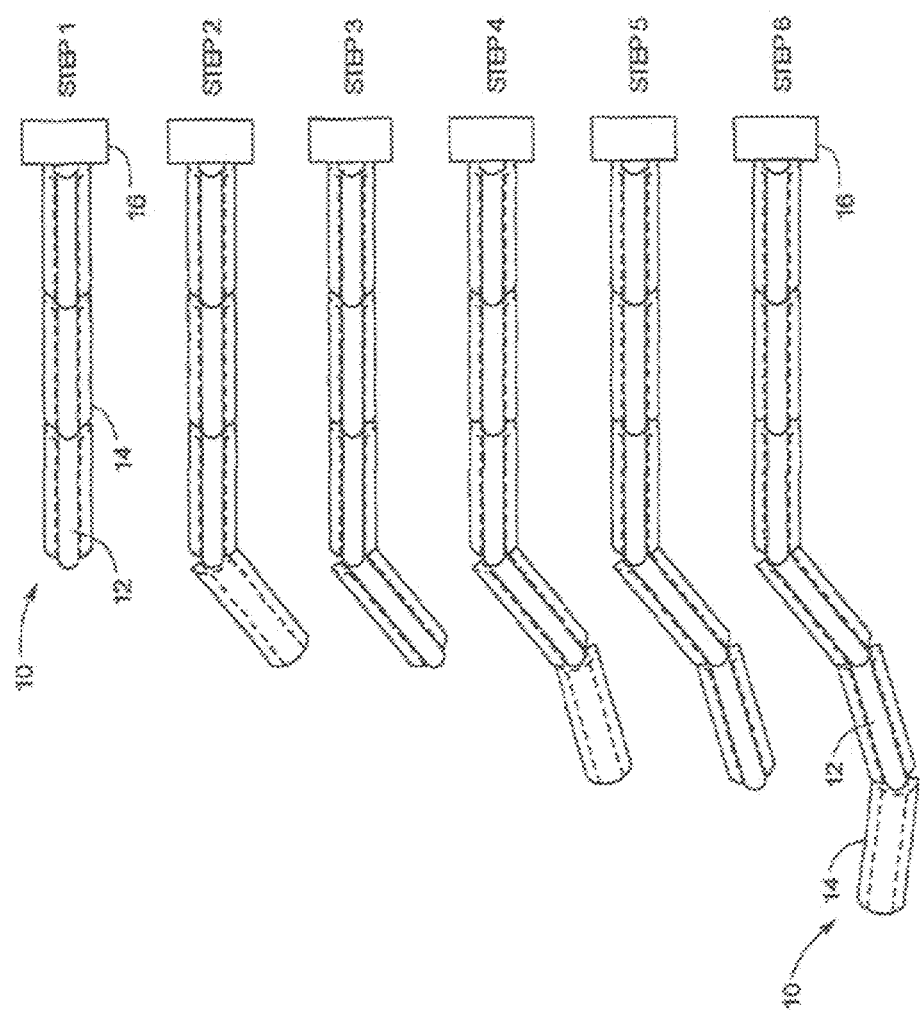

FIGS. 11A-11C are graphic demonstrations of a highly articulated probe device, according to embodiments of the present inventive concepts. A highly articulated robotic probe 10, according to the embodiment shown in FIGS. 11A-11C, comprises essentially two concentric mechanisms, an outer mechanism and an inner mechanism, each of which can be viewed as a steerable mechanism. FIGS. 11A-11C show the concept of how different embodiments of the probe 10 operate. Referring to FIG. 11A, the inner mechanism can be referred to as a first mechanism, an inner core or inner core mechanism 12. The outer mechanism can be referred to as a second mechanism, an outer sleeve or outer sleeve mechanism 14. Each mechanism can alternate between being rigid and limp. In the rigid mode or state, the mechanism is just that—rigid. In the limp mode or state, the mechanism is highly flexible and thus either assumes the shape of its surroundings or can be re-shaped. It should be noted that the term "limp" as used herein does not necessarily denote a structure that passively assumes a particular configuration dependent upon gravity and the shape of its environment; rather, the "limp" structures described in this application are capable of assuming positions and configurations that are desired by the operator of the device, and therefore are articulated and controlled rather than flaccid and passive.

In some embodiments, one mechanism starts limp and the other starts rigid. For the sake of explanation, assume the outer sleeve 14 is rigid and the inner core 12 is limp, as seen in step 1 in FIG. 11A. Now, the inner core 12 is both pushed forward by a feeding mechanism 16, described below, and its "head" or distal end is steered, as seen in step 2 in FIG. 11A. Now, the inner core 12 is made rigid and the outer sleeve 14 is made limp. The outer sleeve 14 is then pushed forward until it catches up or is coextensive with the inner core 12, as seen in step 3 in FIG. 11A. Now, the outer sleeve 14 is made rigid, the inner core 12 limp, and the procedure then repeats. One variation of this approach is to have the outer sleeve 14 be steerable as well. The operation of such a device is illustrated in FIG. 11B. In FIG. 11B it is seen that each mechanism is capable of catching up to the other and then advancing one link beyond. According to one embodiment, the outer sleeve 14 is steerable and the inner core 12 is not. The operation of such a device is shown in FIG. 11C.

In medical applications, once the probe 10 arrives at a desired location, the operator, typically a surgeon, can slide one or more tools through one or more working channels of outer sleeve 14, inner core 12, or one or more working channels formed between outer sleeve 14 and inner core 12, such as to perform various diagnostic and/or therapeutic procedures. In some embodiments, the channel is referred to as a working channel that can, for example, extend between first recesses formed in a system of outer links and second recesses formed in a system of inner links. Working channels may be included on the periphery of probe 10, such as working channels comprising one or more radial projections extending from outer sleeve 14, these projections including one or more holes sized to slidingly receive one or more tools.

In addition to clinical procedures such as surgery, probe 10 can be used in numerous applications including but not limited to: engine inspection, repair or retrofitting; tank inspection and repair; spying and surveillance applications; bomb disarming; inspection or repair in tightly confined spaces such as submarine compartments or nuclear weapons; structural inspections such as building inspections; hazardous waste remediation; biological sample recovery such as anthrax recovery; and combination of these. Clearly, the device of the present disclosure has a wide variety of applications and should not be taken as being limited to any particular application.

Inner core 12 and/or outer sleeve 14 are steerable and inner core 12 and outer sleeve 14 can each be made both rigid and limp, allowing probe 10 to drive anywhere in three-dimensions while being self-supporting. Probe 10 can "remember" each of its previous configurations and for this reason, probe 10 can retract from and/or retrace to anywhere in a three dimensional volume such as the intracavity spaces in the body of a patient such as a human patient.

Particularly when the links are made rigid by the cables after having been steered, the significant forces applied to the links through the cables will act upon, or act with respect to, the base structure of the robot driving mechanism. These forces can potentially induce unpredictable and otherwise undesired movement between the base structure of the robot and the robot arm, particularly its distal end, and the various components therein. Where precise control of motion and/or stability of the robot is desired, it is imperative to resist these forces to avoid such undesired movement.

FIG. 1A is a perspective illustrative view of an articulating probe system 100 according to an embodiment of inventive concepts. In an embodiment, a patient table 110 is integrated with an adjustable base stand 120 to which an articulating robot probe 175 is connected, typically through a rotatable, removable connection. The articulating robot probe 175 includes probe arm 315, typically a link assembly including a plurality of inner and outer links as described in reference to FIGS. 11A-11C. Robot probe 175 is operably connected to a console system 150 configured for driving probe arm 315, such connection typically including electrical wires or optical fibers for transmission of power and/or data, or mechanical transmission conduits such as mechanical linkages or pneumatic/hydraulic delivery tubes. The articulating robot probe 175 includes a feeder assembly 300 that feeds an articulating robot probe arm such as is described above in reference to FIGS. 11A-11C. In an embodiment, the feeder assembly 300 is a detachable component that connects with a base unit 200, such as base unit 200 described in reference to FIG. 7A. In other embodiments, the feeder assembly 300 and the base unit 200 are a unitary structure not designed to be readily detachable. In other embodiments, various components of the system such as, for example, the feeder assembly 300 is detachable and replaceable.

Figure 1B:
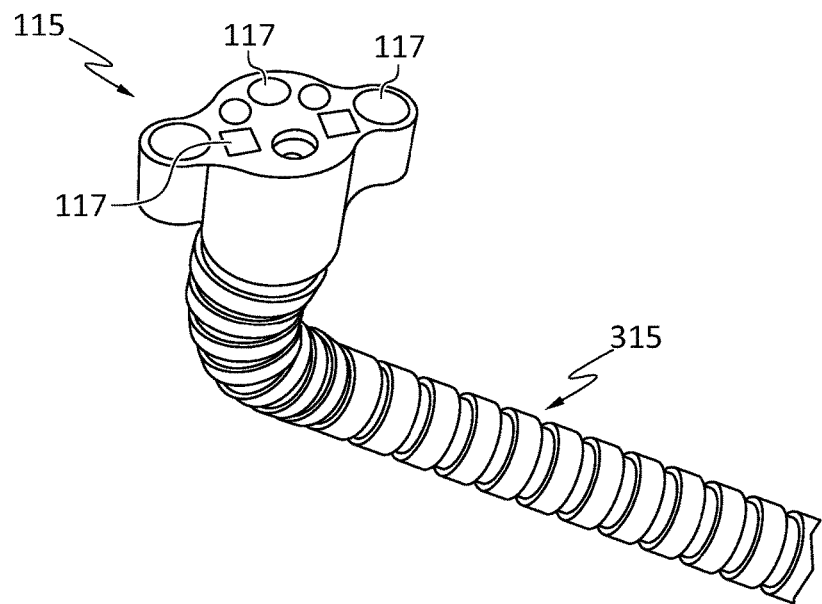
FIG. 1B is a perspective illustrative view of an articulating probe arm according to an embodiment of inventive concepts.
Figure 1C:
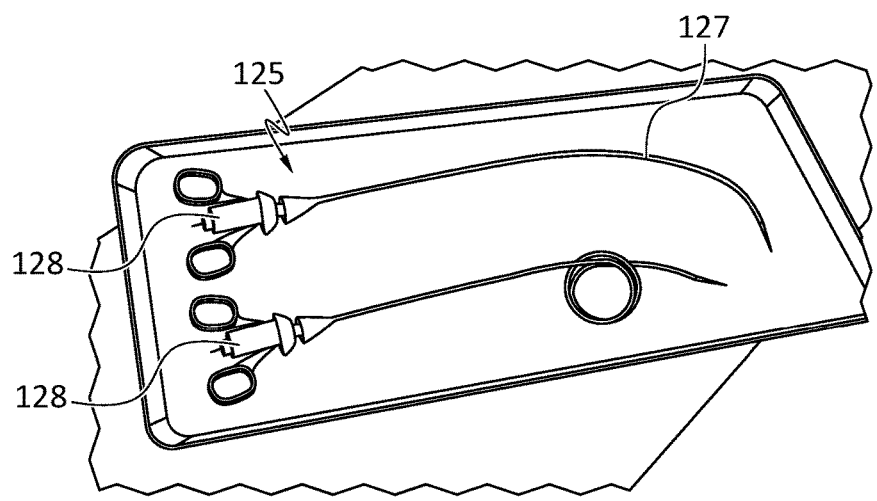
FIG. 1C is a perspective illustrative view of probe tools which can be integrated with an articulating probe arm according to an embodiment of inventive concepts.

FIG. 1B is a perspective illustrative view of the distal end of articulating probe 175 according to an embodiment of inventive concepts. In an embodiment, a probe arm 315, such as a link assembly including a plurality of inner and outer links as described in reference to FIGS. 11A-11C, includes a distal end 115 with a plurality of working channels 117. As described previously herein the working channels can support a variety of tools including, for example, cameras, light sources, and surgical tools such as cutters, graspers, scissors, energy appliers, suturing assemblies, biopsy removal elements, etc. Tools may be slidingly received by the working channels 117 or they may be fixedly inserted in a working channel 117, such as during a manufacturing process. FIG. 1C is a perspective illustrative view of probe tools 125 which can be integrated with an articulating probe arm according to an embodiment of inventive concepts. Probe tools 125 include an elongate conduit 127 which may be integrated with and extend through one of the working channels 117, for example, working channels 117 located within or mounted to the periphery of probe arm 315. In an embodiment, probe tools 125 include hand-operable controls 128 such as, for example, controls operably connected to one or more sharp surfaces positioned on the distal end of conduit 127, such as for cutting tissue with a tool extending through working channel 117.

Figure 2A:
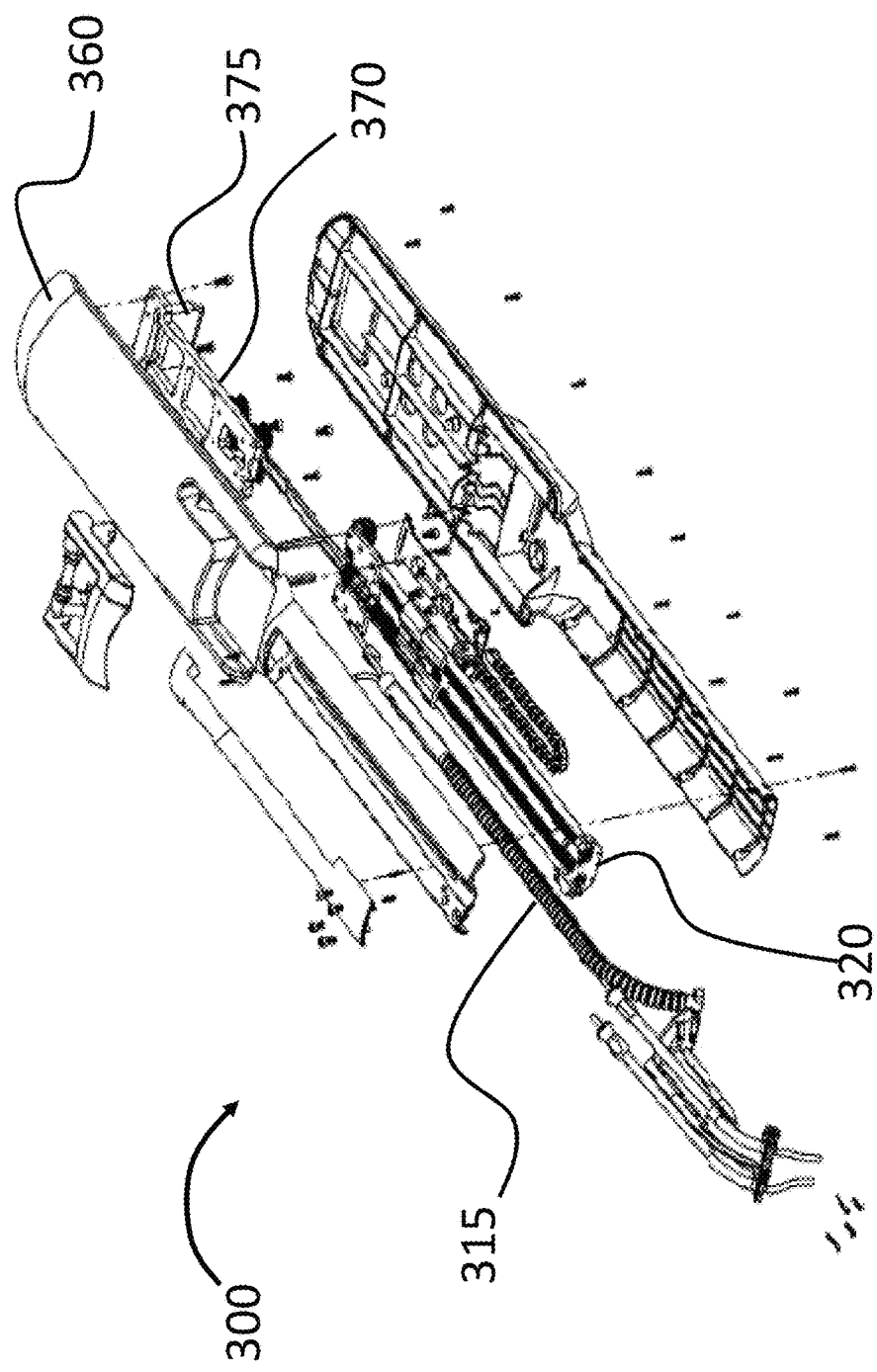
FIG. 2A is an exploded design schematic of a detachable feeder system for an articulating probe arm according to an embodiment of inventive concepts.
Figure 2B:
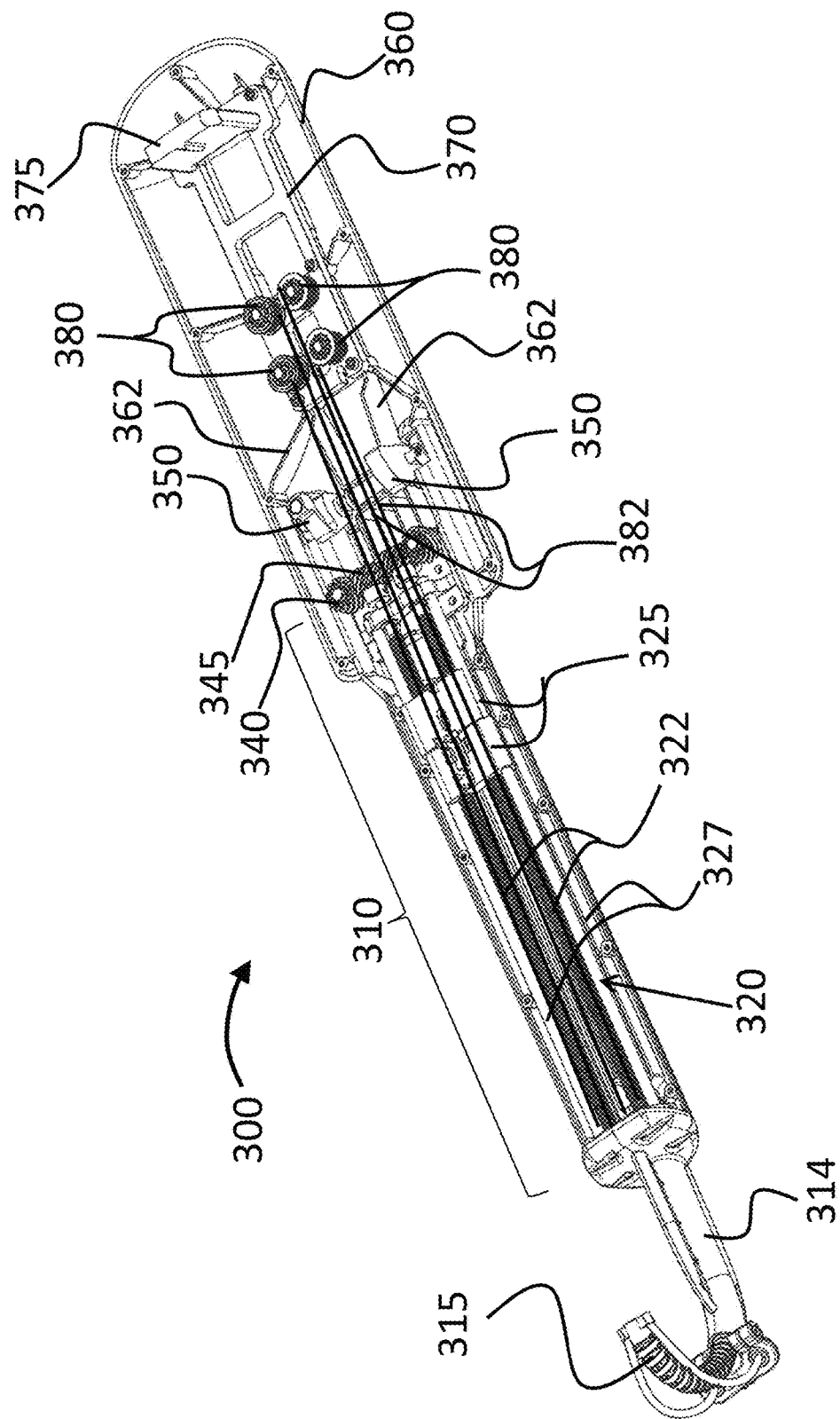
FIG. 2B is an illustrative internal view of a feeder system according to an embodiment of inventive concepts.

FIG. 2A is an exploded design schematic of a detachable feeder system 300 for an articulating probe, such as articulating probe 175 of FIGS. 1A-1C, according to an embodiment of inventive concepts. FIG. 2B is an illustrative internal view of a feeder system according to an embodiment of inventive concepts. In an embodiment, the feeder system 300 includes a housing 360 having a stabilization plate 370, to which cable bobbins 380 are mounted. Housing 360 is typically an injection molded, plastic housing, such as a reinforced plastic housing. In an embodiment, the stabilization plate 370 is mounted to housing 360 proximate reinforced housing ribs 362. In an embodiment, cables 382 extend through a probe arm 315 comprising both inner and outer links (e.g., the links of inner core 12 and outer sleeve 14 of FIGS. 11A-11C). In an embodiment, the cables 382 can be used to steer and/or releasably tighten to "lock"/ stiffen either or both of the inner or outer links such as described above. In an embodiment, one or more cables 382 can be used to lock the links and two or more cables 382 can be used to steer the links. For example, three cables 382 can be designated for steering the links of outer sleeve 14 of FIGS. 11A-11C in three dimensions. These three cables 382 can also be used for locking the outer sleeve. The remaining cable(s) 382 can be used for locking the links of inner core 12. In an embodiment, when using cables 382 for locking, the forces applied can be distributed over cables 382. For example, if a 36 lb force is applied for locking the outer sleeve 14 connected to three cables, a force of 12 lbs can be applied to each of the connected cables. In an embodiment, three of the bobbins 380 are configured to control the outer links, such as to steer, feed cable for probe arm 315 advancement, retract cable for probe arm 315 retraction, transition probe arm 315 from a limp to a rigid state (e.g. to lock), and to transition probe arm 315 from a rigid to a limp state (e.g. to become flexible). In this embodiment, one bobbin 380 is typically used to control the inner links, such as to feed cable for probe arm 315 advancement, retract cable for probe arm 315 retraction, transition probe arm 315 from a limp to a rigid state (e.g. to lock), and to transition probe arm 315 from a rigid to a limp state (e.g. to become flexible). In some embodiments, the forces exerted by the bobbins 380 can exceed 1, 10, 30 and/or 50 pounds, such as to lock the attached inner or outer links of probe arm 315. In configurations in which four cables are used to steer and lock probe arm 315, collective forces exerted by the bobbins can exceed 95 pounds, such as when 50 pounds is applied to lock the inner links (e.g. with a single cable) and 15 pounds per cable is used to lock the outer links (e.g. with three cables). In various embodiments, the amount of force applied is related to the size (including diameter and length) of the links of the inner core 12 and outer sleeve 14 and also to the smoothness of the steering of the links. Greater force may be necessary to lock and stabilize a set of larger and/or longer links, including when the links are extended or retracted with respect to each other.

Figure 7A:
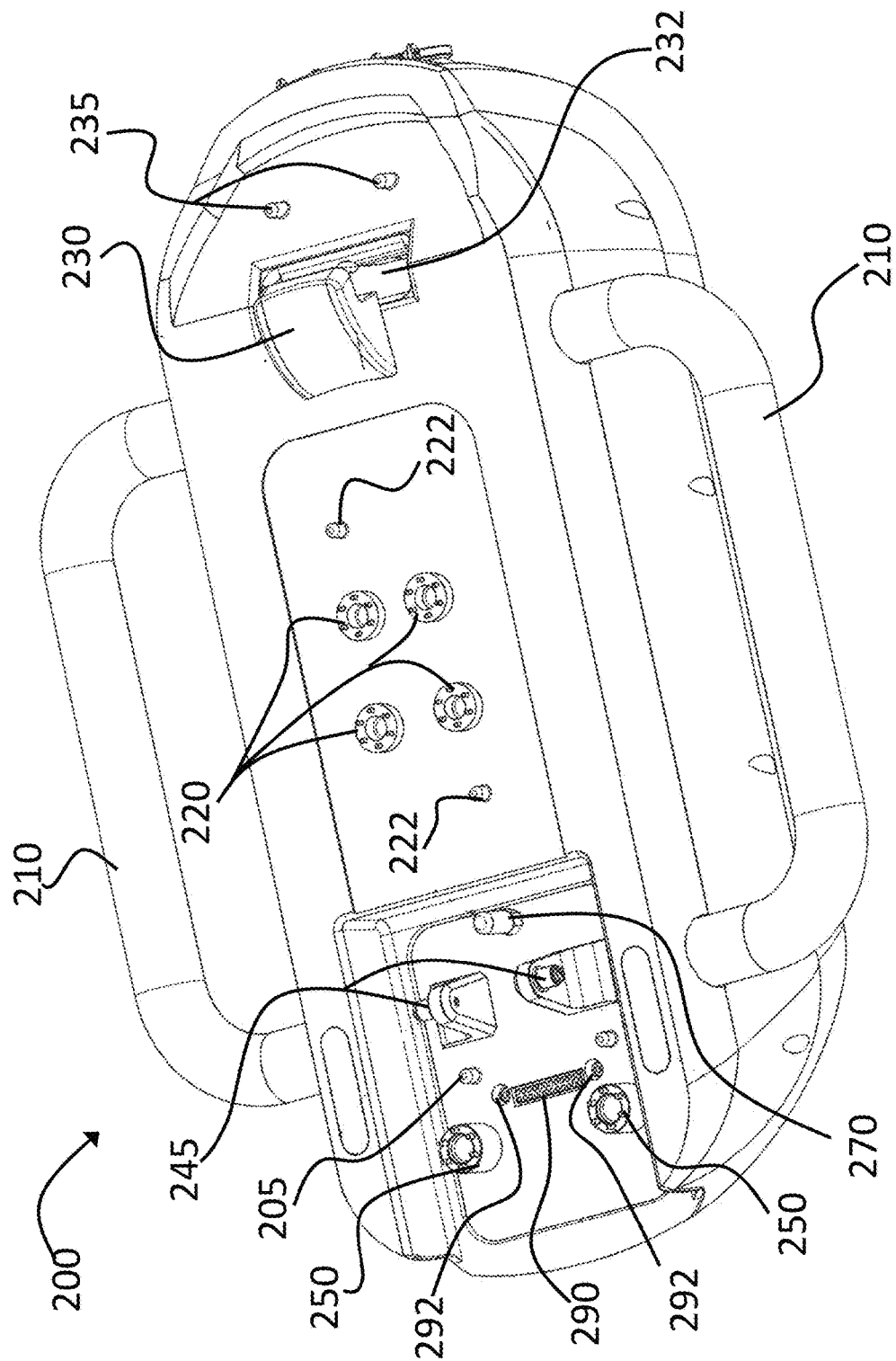
FIG. 7A is an illustrative perspective view of a base unit of a force-transfer driving assembly according to an embodiment of inventive concepts.

A heel plate 375 is fixedly attached to the stabilization plate 370 and can lockably engage with a base unit (e.g., base unit 200 shown and described with respect to FIG. 7A). Latches 350 are also attached to the housing 360 which are arranged to lockably engage with a base unit (e.g., base unit 200 shown and described with respect to FIG. 7A). In an embodiment, latches 350 can articulate and are spring loaded, so as to rotate downward upon engaging latch prongs (such as prongs 245 of FIG. 7A). In an embodiment, the spring loaded latches 350 provide up to about 20 pounds of tension. The heel plate 375 and latches 350 interlock with a base unit (e.g., base unit 200 of FIG. 7A) and thereby stabilize and aid in the resistance of undesired motion, including lateral motion, of the feeder system and base unit during the transfer of power to the probe arm 315 such as via bobbins 380. In an embodiment, the feeder system 300 is configured to be detachable from a base unit, such as to be cleaned or replaced with another feeder system (e.g., where a robot probe arm is exposed to biological or toxic materials).

The carriage drive segment 310 is attached distally to a reinforced introducer 314, further described below with reference to FIG. 4C, through which probe arm 315 extends and is used for guiding the probe arm's initial path through or toward a target area such as, for example, when introducer 314 comprises an outer surface similar to a body cavity shape found in a majority of patients. Probe arm 315 may be configured to rapidly advance through introducer 314, prior to fine motion control used after probe arm 315 exits introducer 314.

Figure 3A:
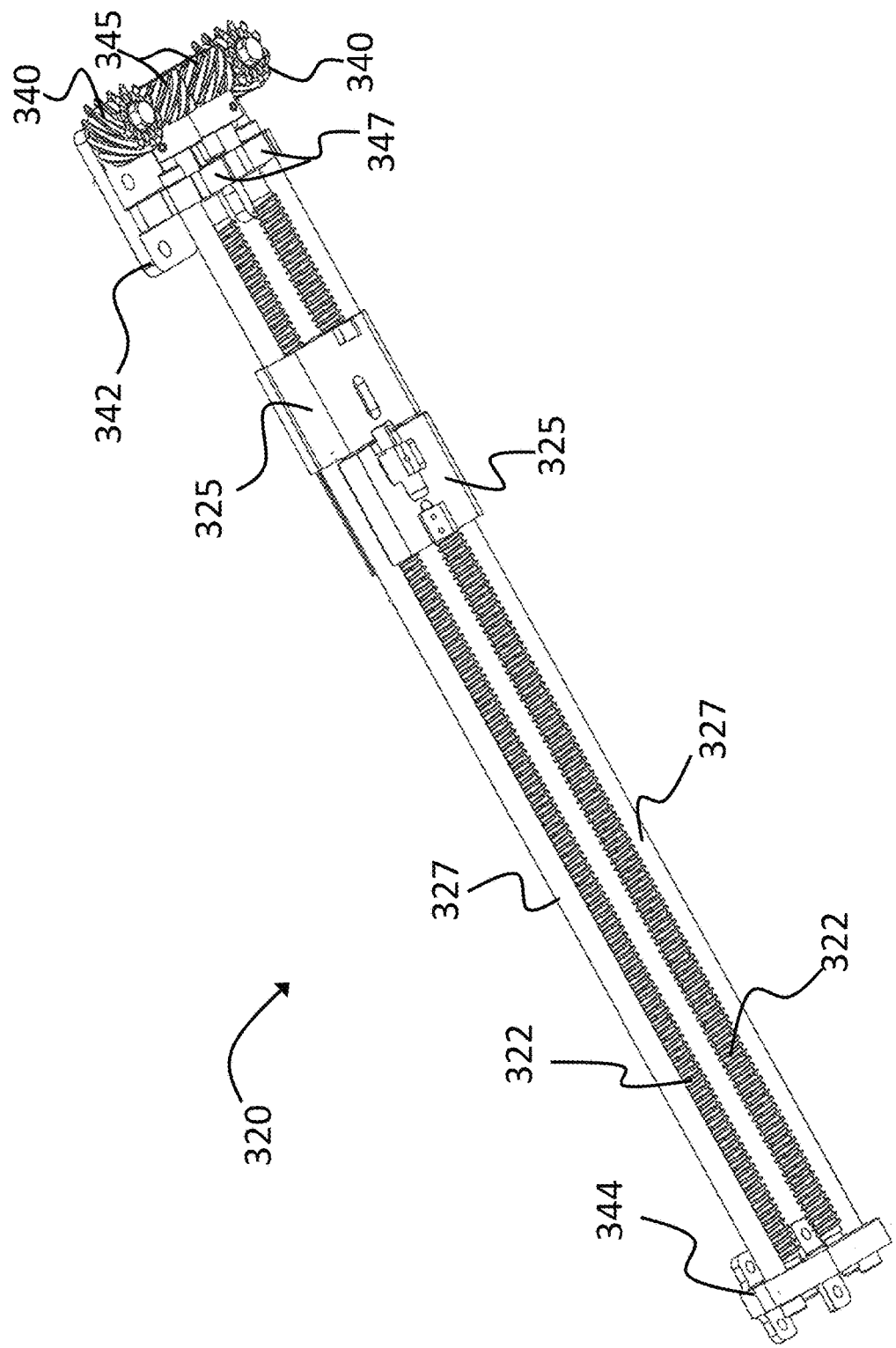
FIG. 3A is an illustrative perspective view of a force-transfer driving assembly of a feeder system according to an embodiment of inventive concepts.
Figures 3B, 3C:
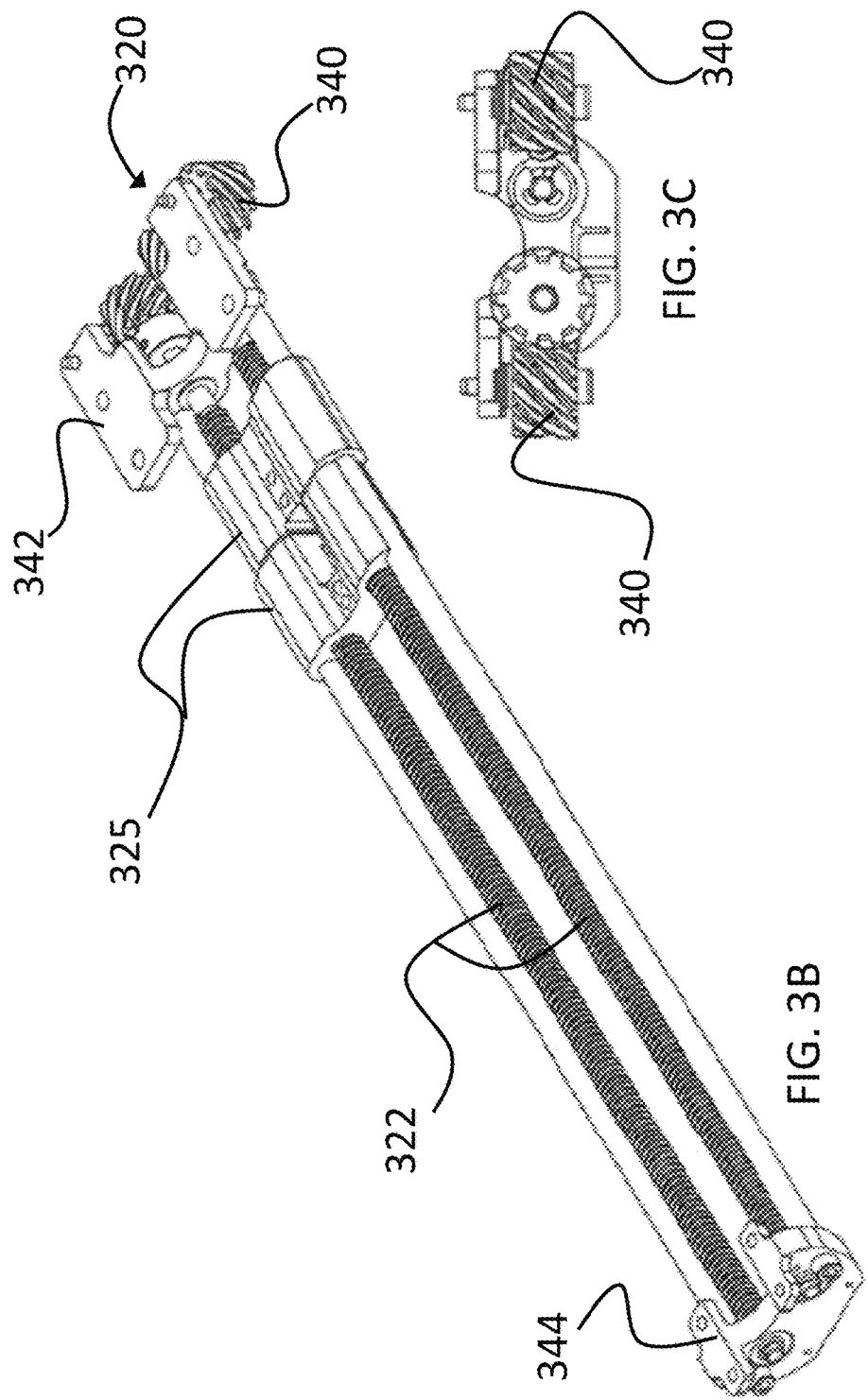
FIG. 3B is a design schematic of a force-transfer driving subassembly of a feeder system according to an embodiment of inventive concepts.
FIG. 3C is an illustrative side-perspective view of a ninety-degree gear transfer subassembly of the force-transfer driving assembly of FIG. 3B.

Referring to FIGS. 2A, 2B and FIG. 3A, an illustrative perspective view of a force-transfer driving subassembly 320 of the feeder system 300 is shown. Feeder system 300 includes a carriage drive segment 310 which is configured to independently drive two carriages 325 along two lead screws 322. In an embodiment, one carriage 325 drives an outer set of links and one carriage 325 drives an inner set of links such as described, for example, with respect to FIGS. 11A-11C. The lead screws 322 are driven by a ninety-degree gear assembly including gears 340 and 345. In an embodiment, gears 340 and 345 include helical threads so as to increase overall contact between them and further stabilize force transfer between a base unit (e.g., base unit 200 of FIG. 7A) and articulating probe arm 315. In an embodiment, gears 340 engage rotary drives such as rotary drives 250 shown in FIG. 7A and further described below. Lead screws 322 are secured within bearing mounting blocks 342 and 344 that are mounted to housing 360. In an embodiment, bearing mounting block 342 includes thrust bearings 347 for further stabilizing the force transfer between gears 345 and lead screws 322. In an embodiment, carriages 325 include grooves to slidably ride upon guide rails 327, which aid in ensuring linear movement of carriages 325 and providing additional stabilization of the assembly 320, feeder system 300, and probe arm 315, so as to resist undesired movement during force-transfer, such as undesired torqueing or compression of feeder system 300. Guide rails 327 can further prevent undesired relative movement between the carriages, particularly when unequal forces are applied to them. In an embodiment, rails 327 are slidingly received and fixed within bearing blocks 344 and 342 in order to maintain substantially parallel configuration to maintain stability of the feeder system 300. In an embodiment, guide rails 327 are configured to have square, rectangular, round, slotted, or other various cross sectional shapes configured to slidingly engage a receiving portion of carriages 325. In one embodiment, guide rails 327 have a rectangular cross section configured to prevent undesired twisting along one or more axes of feeder system 300 (e.g. the major axis of feeder system 300). The dual screw and rail configuration helps, in particular, to resist twisting and bending of the feeder system. In an embodiment, subassembly 320 is a separate subassembly that is secured into the housing 360 to minimize the deflection of the housing during force transfer, such as when housing 360 comprises a plastic, injection-molded housing. In an embodiment, the carriages 325 include reinforced bushings to engage with the lead screws and/or rails. In an embodiment, the bushings are coated with Teflon or a similarly lubricious material. FIG. 3B is a design schematic of a force-transfer driving subassembly 320 of the feeder system 300 according to an embodiment of inventive concepts. FIG. 3C is an illustrative side-perspective view of a ninety-degree gear transfer subassembly of the force-transfer driving assembly of FIG. 3B.

Figure 3D:
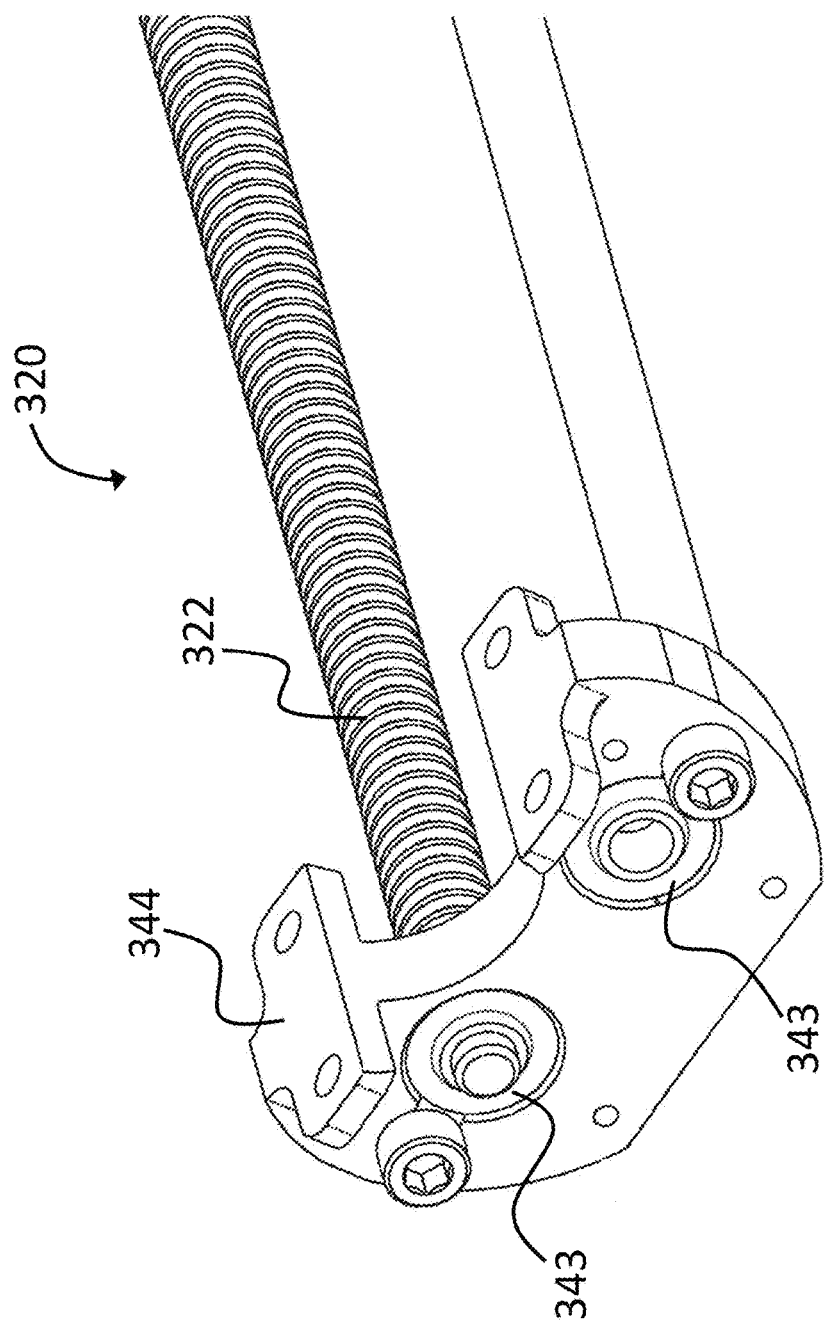
FIG. 3D is another illustrative perspective view of a force-transfer driving assembly of FIG. 3B.
Figure 3E:
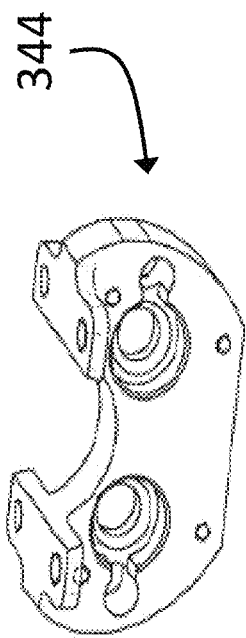
FIG. 3E is an illustrative perspective view of a bearing mounting block for a lead screw of the force-transfer driving assembly of FIGS. 3A-3B according to an embodiment of inventive concepts.

FIG. 3D is another illustrative perspective view of a force-transfer driving subassembly 320 of FIG. 3B, with one lead screw 322 and other components removed for illustrative clarity. In an embodiment, the mounting block 344 includes spherical bearings 343 to help ensure proper alignment between the lead screw 322 and the bearing mounting block 344. FIG. 3E is an illustrative perspective view of a bearing mounting block 344 for a lead screw of the force-transfer driving assembly of FIGS. 3A-3B according to an embodiment of inventive concepts.

Figure 3F:
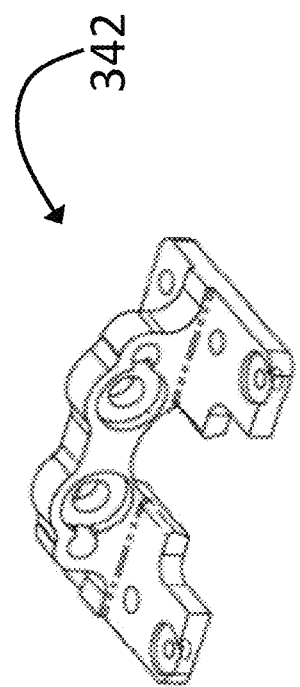
FIG. 3F is an illustrative perspective view of a bearing mounting block for a lead screw of the force-transfer driving assembly of FIGS. 3A-3B according to an embodiment of inventive concepts.

FIG. 3F is an illustrative perspective view of a bearing mounting block 342 for a lead screw 322 of the force-transfer driving assembly 320 of FIG. 3A-3B. As discussed above, in an embodiment, bearing mounting block 342 includes thrust bearings 347 for further stabilizing the force transfer between gears 345 and lead screws 322.

Figure 4A:
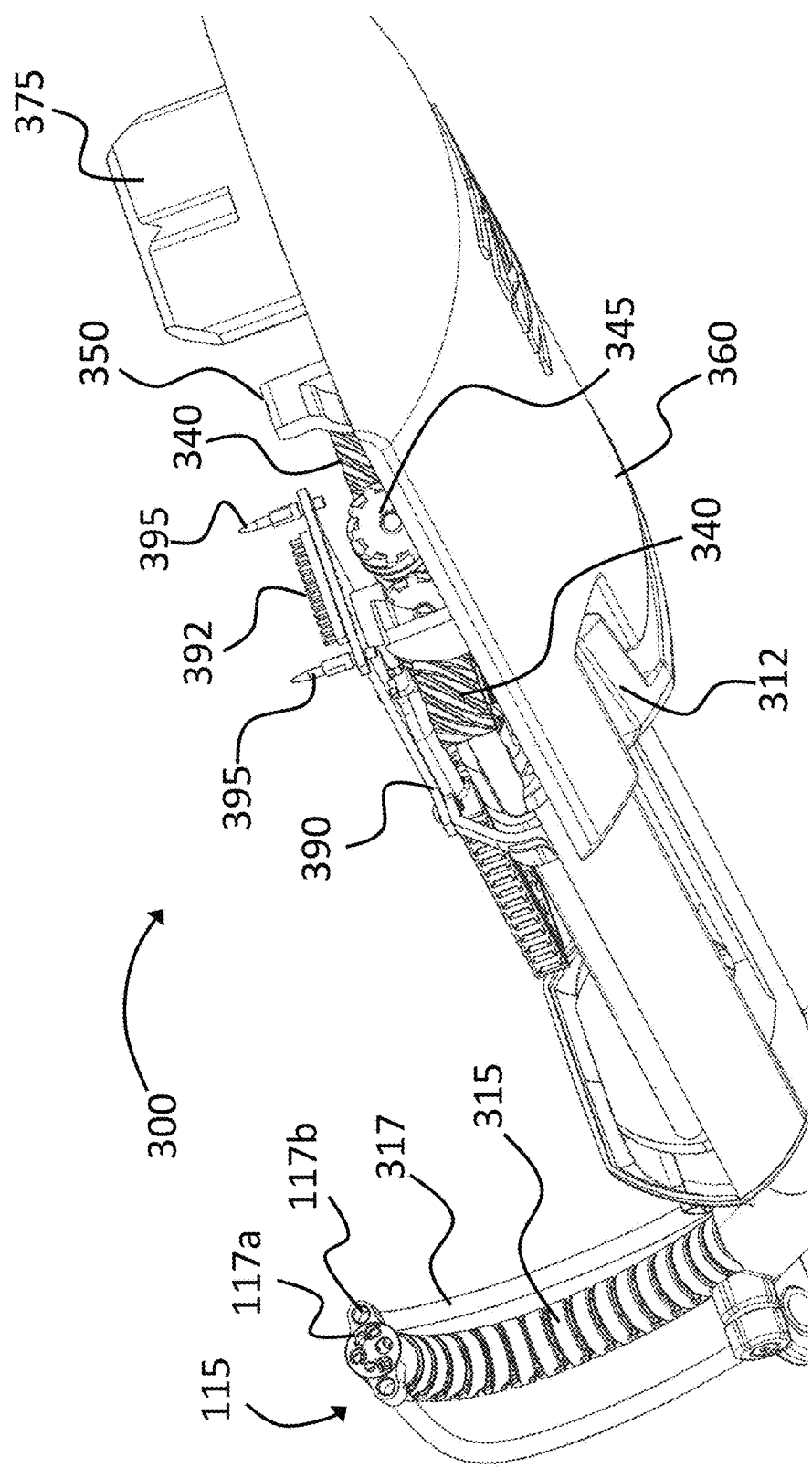
FIG. 4A is an illustrative internal perspective view of the feeder system of FIG. 2B according to an embodiment of inventive concepts.

FIG. 4A is an illustrative internal perspective view of the feeder system 300 according to an embodiment of inventive concepts. System 300 can comprise components similar to those described hereabove. In an embodiment, a floating mounting block 390 supports an electrical connector 392 and aids in electrically isolating connector 392 from a chassis of a base unit, for example base unit 200 of FIG. 7A. Alignment pins 395 help ensure alignment of the electrical connector 392 and may also provide additional motion resistant stabilization. In an embodiment, the alignment pins 395 are tapered so as to improve insertion, alignment and motion resistance. Electrical and/or fiber optic connections can be used, for example, to provide power to and/or transmission signals to or from various components connected to the probe arm 315 including but not limited to one or more elements integrated into distal end 115 of probe arm 315 such as one or more elements selected from the group consisting of: a camera; a light such as an LED; an electrode such as an electrode configured to deliver radiofrequency energy; and combinations of these. A gripping and latch release handle 312 permits an operator to releasably engage/connect the feeder system with a base unit. In one embodiment, handle 312 is configured to rotate latches 350, such as to engage one or more pins of a base unit, such as pins 245 of base unit 200 of FIG. 7A.

Probe arm 315 typically includes one or more working channels, such as internal working channels 117a and external, sideport working channels 117b. Sideport working channels 117b are connected to guide tubes 317, configured to receive the distal portions of one or more elongate tools such as those described in reference to FIG. 1C.

Figure 4B:
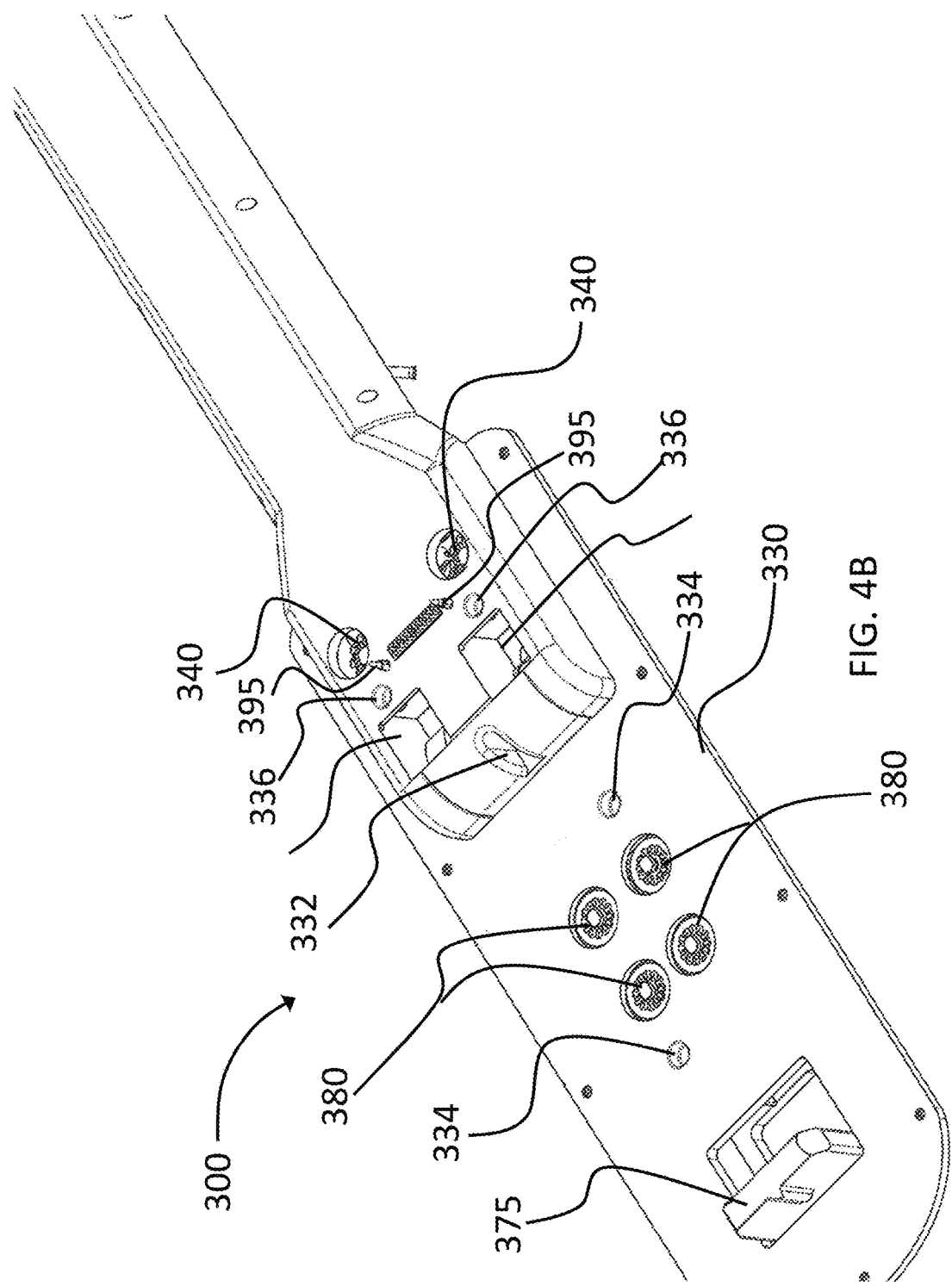
FIG. 4B is an illustrative external perspective view of the feeder system of FIG. 4A according to an embodiment of inventive concepts.

FIG. 4B is an illustrative external perspective view of the feeder system 300 of FIG. 4A according to an embodiment of inventive concepts, including a housing cover 330. Housing cover 330 includes various openings, recesses, and slots for interfacing, securing, and/or stabilizing attachment of the feeder system 300 to a base unit (e.g., base unit 200). Receiving holes 336, 332 and 334, for example, are configured to engage pins 205, 270, and 222, respectively, of a base unit 200 such as shown in FIG. 7A and provide additional stability and resistance to movement between the feeder system 300 and base unit 200. Alternatively or additionally, holes 336, 332 and/or 334 may be configured to allow pins 205, 270 and/or 222, respectively to pass therethrough, and engage with one or more other components of feeder system 300, such as one or more stabilizing metal plates of feeder system 300.

Figure 4C:
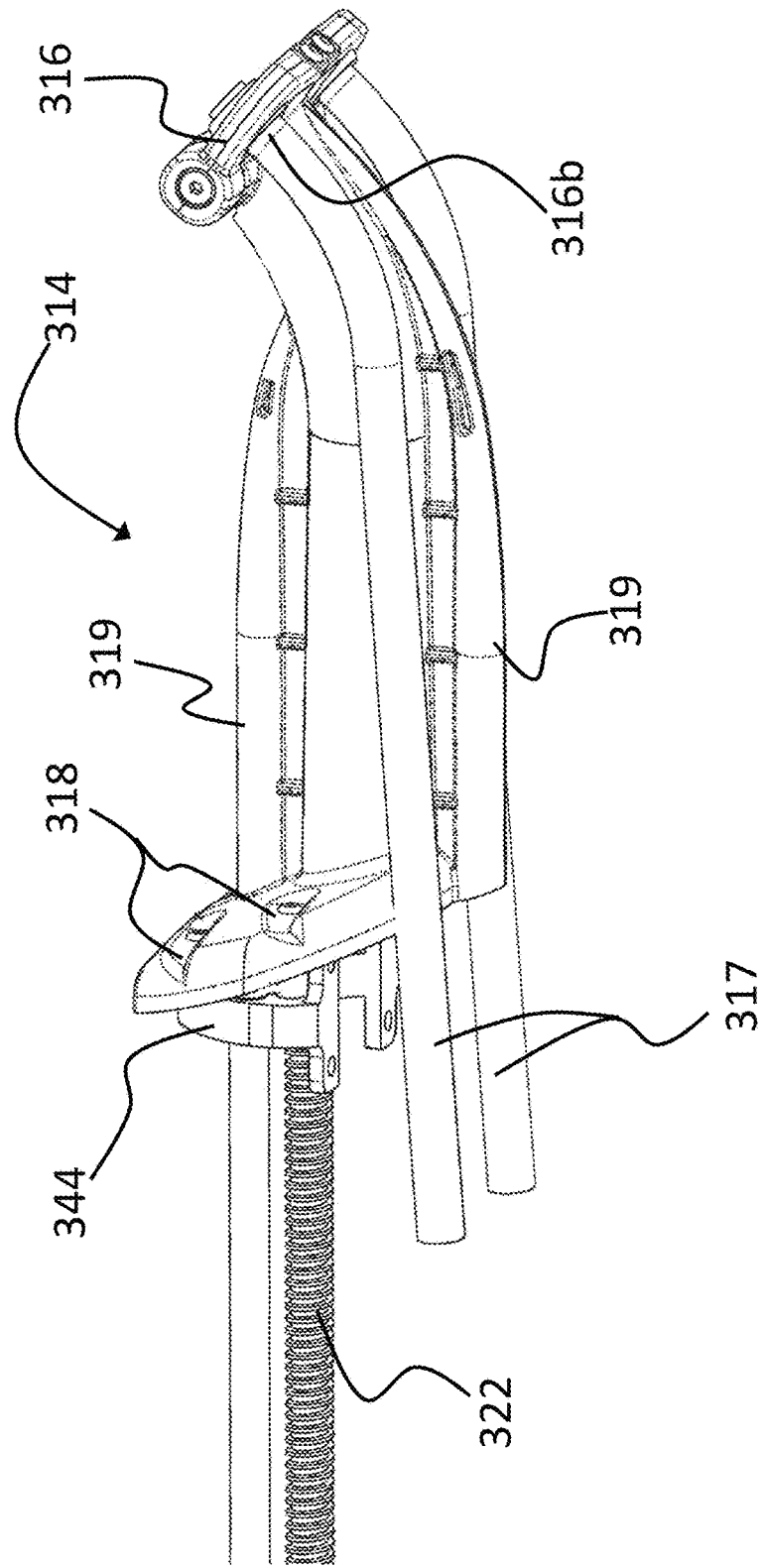
FIG. 4C is an illustrative perspective view of an introducer assembly according to an embodiment of inventive concepts.

FIG. 4C is an illustrative perspective view of an introducer assembly 314 according to an embodiment of inventive concepts. Introducer assembly 314 is mounted to mounting block 344 via mounting screws 318 and includes stabilization ribs 319 to prevent bending and twisting of the introducer assembly 314 and any probe arm and attached tools guided therethrough. Tool guides 317 are rotatably connected to the distal end of introducer 314 at ball joint 316b of collar 316 which, in embodiments, is reinforced to further stabilize the introducer assembly.

Figure 5A:
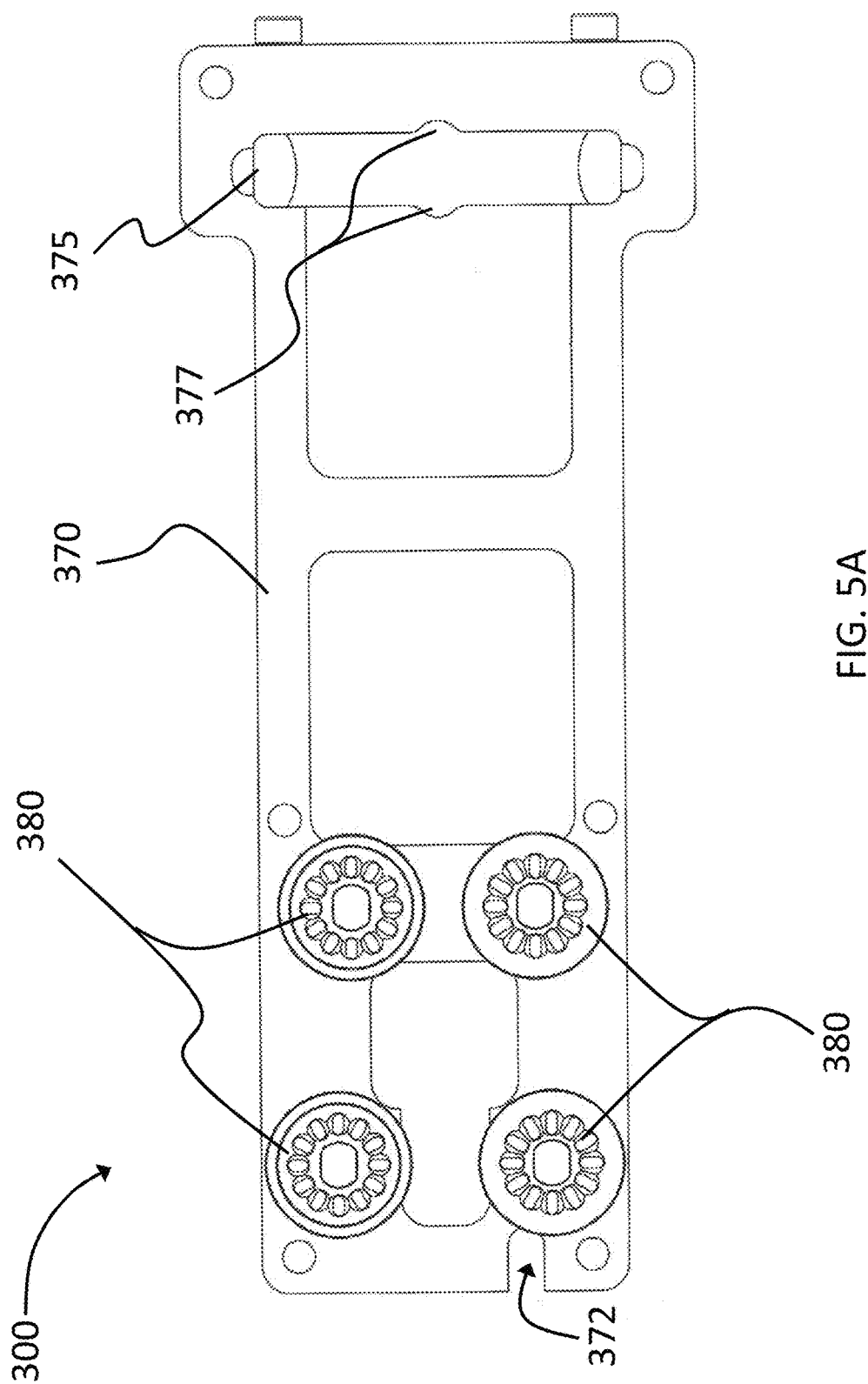
FIG. 5A is an illustrative top view of a stabilizing plate for a force-transfer driving assembly of a feeder system according to an embodiment of inventive concepts.
Figure 5B:
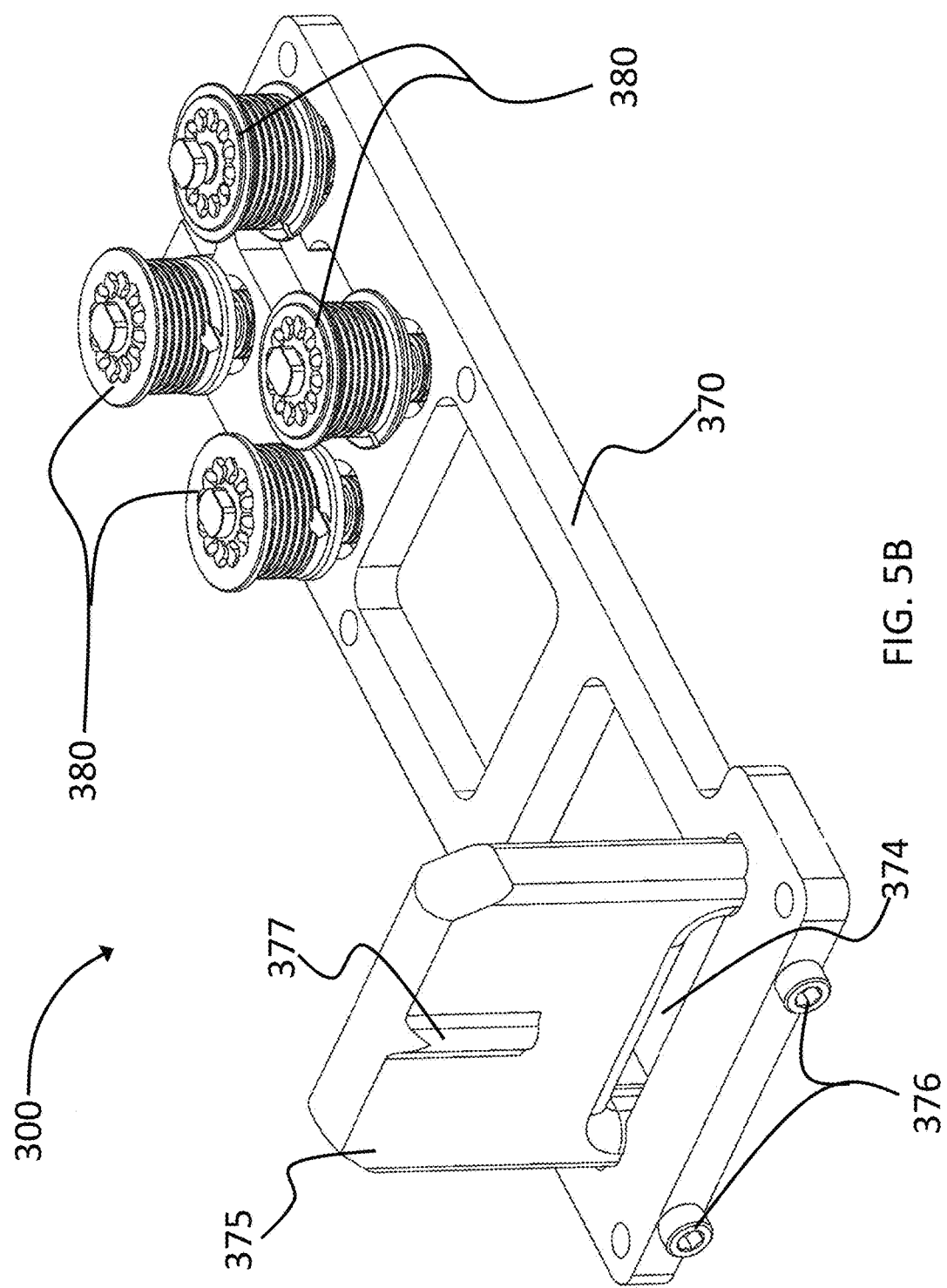
FIG. 5B is a perspective view of the stabilizing plate of FIG. 5A.
Figure 5C:
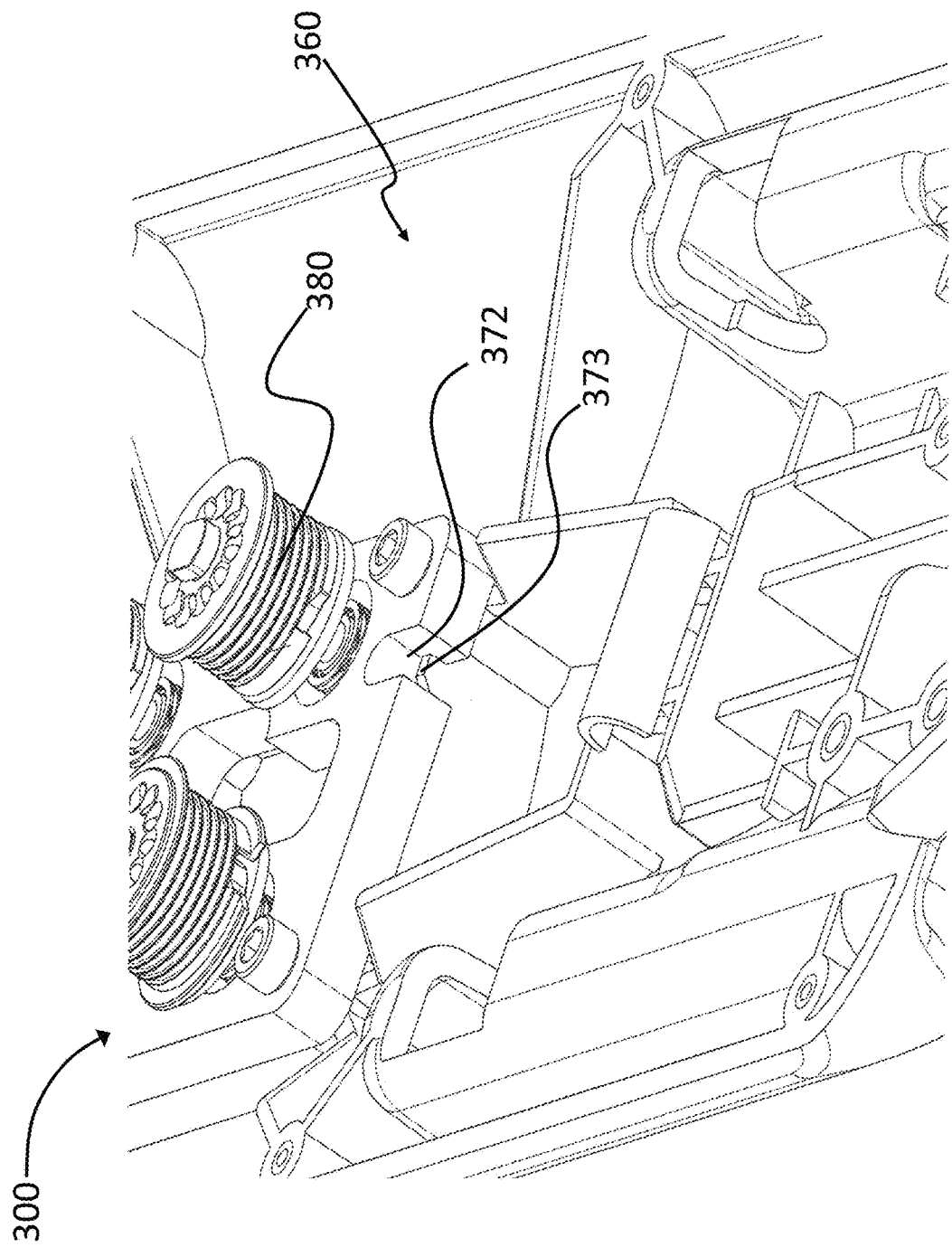
FIG. 5C is a perspective partial view of the stabilizing plate of FIG. 5A integrated within a feeder assembly according to an embodiment of inventive concepts.
Figure 5D:
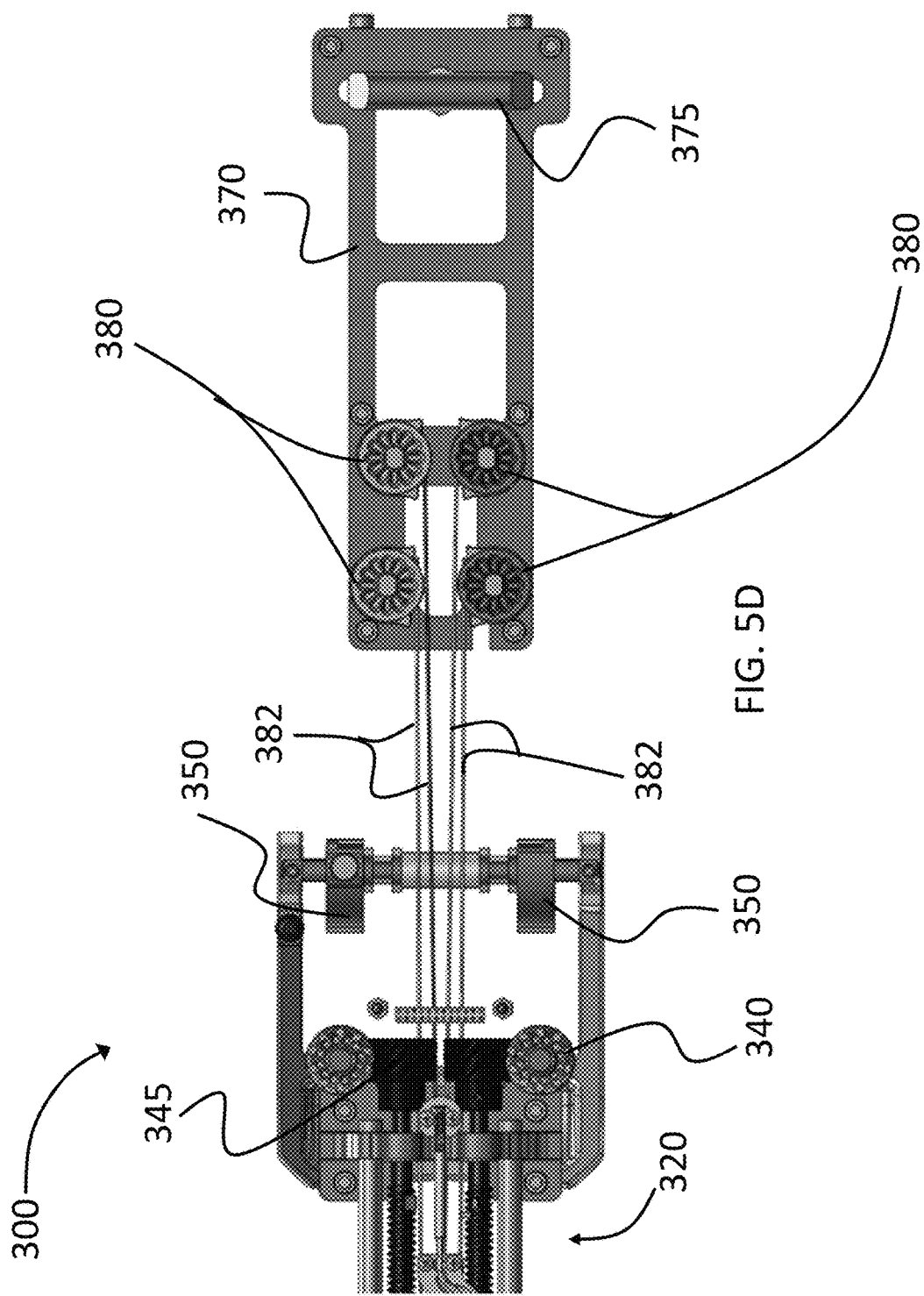
FIG. 5D is an illustrative view of a bobbin and cable feeding mechanism arranged with the stabilization plate of FIG. 5A.

FIG. 5A is another illustrative top view of a stabilizing plate 370 for a force-transfer driving assembly of a feeder system 300 according to an embodiment of inventive concepts. FIG. 5B is a perspective view of the stabilizing plate 370 of FIG. 5A. FIG. 5C is a perspective partial view of the stabilizing plate of FIG. 5A integrated within a feeder assembly according to an embodiment of inventive concepts. FIG. 5D is an illustrative view of a bobbin and cable feeding mechanism arranged with the stabilization plate 370 of FIG. 5A. In an embodiment, the mounted heel plate 375 includes aligning ribs 377 which improve alignment and motion resistance at the attachment of the feeder assembly 300 to a base unit, for example base unit 200 of FIG. 7A. In an embodiment, the stabilizing plate 370 includes a mating surface 372 that serves as an alignment guide, mating with a zero draft projection 373 of housing 360 when assembling the stabilization plate 370 with feeder system assembly 300 (as shown in FIG. 5C) so as to allow precision fitting and minimal gap tolerances between the fitted parts, thereby minimizing undesired movement between the parts. Screws 376 align, attach, and stabilize heel plate 375 with respect to stabilizing plate 370. Recess 374 engages an articulating latching tongue of a base unit, such as latching tongue 230 of Fig. base unit 200 of FIG. 7A.

Figure 6:
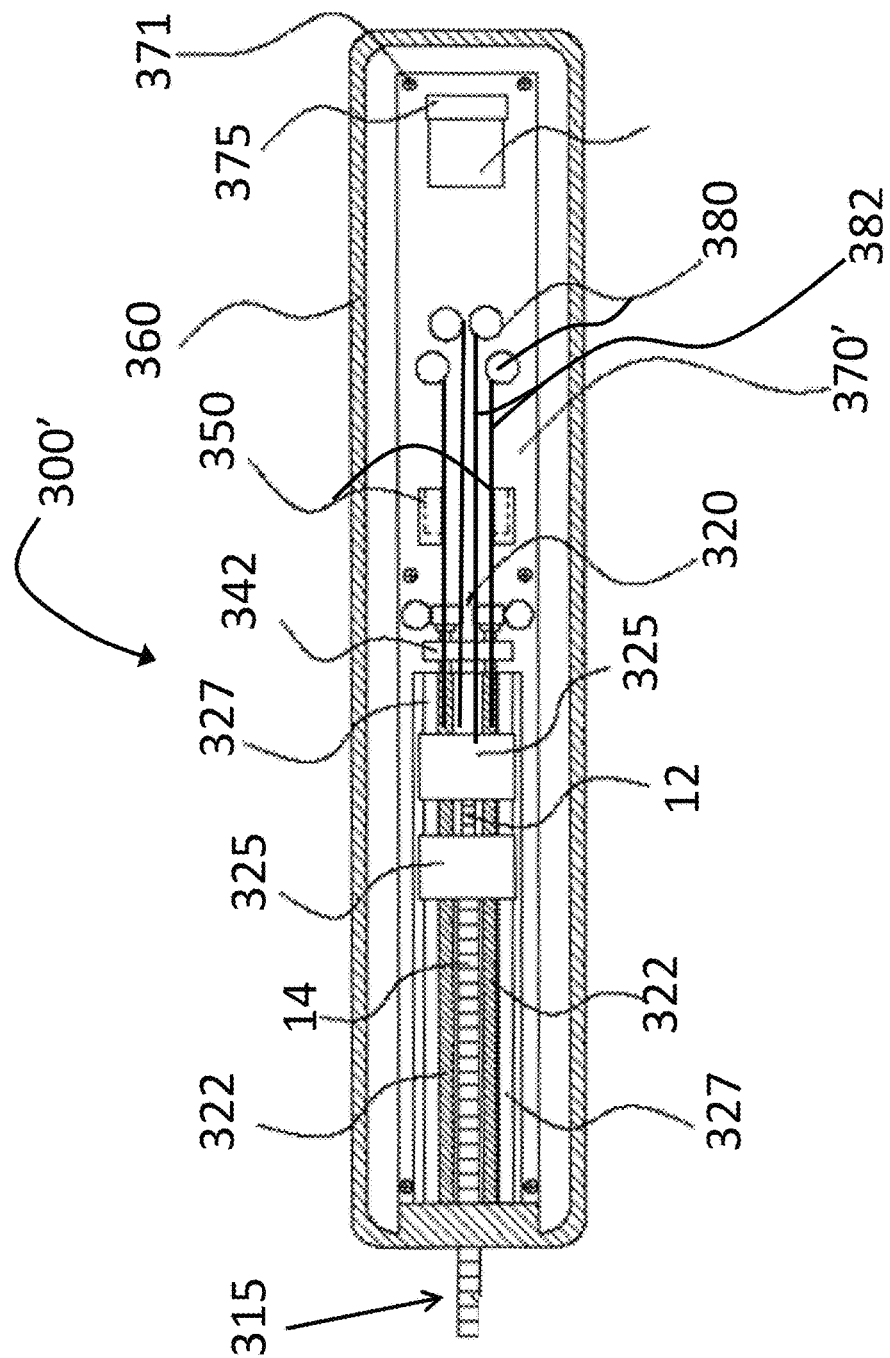
FIG. 6 is a top illustrative view of an elongate stabilizing plate integrated within a feeder assembly according to an embodiment of inventive concepts.

FIG. 6 is a top illustrative view of an elongate stabilizing plate 370' integrated within a feeder assembly 300' according to an embodiment of inventive concepts. In an embodiment, a single stabilizing mounting plate 370' mounts together with heel plate 375, bobbins 380, a force-transfer drive subassembly 320, and probe arm 315, such as to minimize twisting, compression and other undesired displacements. Probe arm 315 comprises outer links 14 and inner links 12, such as those described in reference to FIGS. 11A-11C. A unitary mounting plate 370' can provide additional resistance to bending or twisting of the feeder assembly 300' and can simplify construction of the feeder assembly 300'. Stabilizing plate 370' is secured to housing 360 via mounting screws 371. Feeder assembly 300' includes other components, such as those with the same reference numbers as are described above in reference to feeder assembly 300.

Figure 7B:
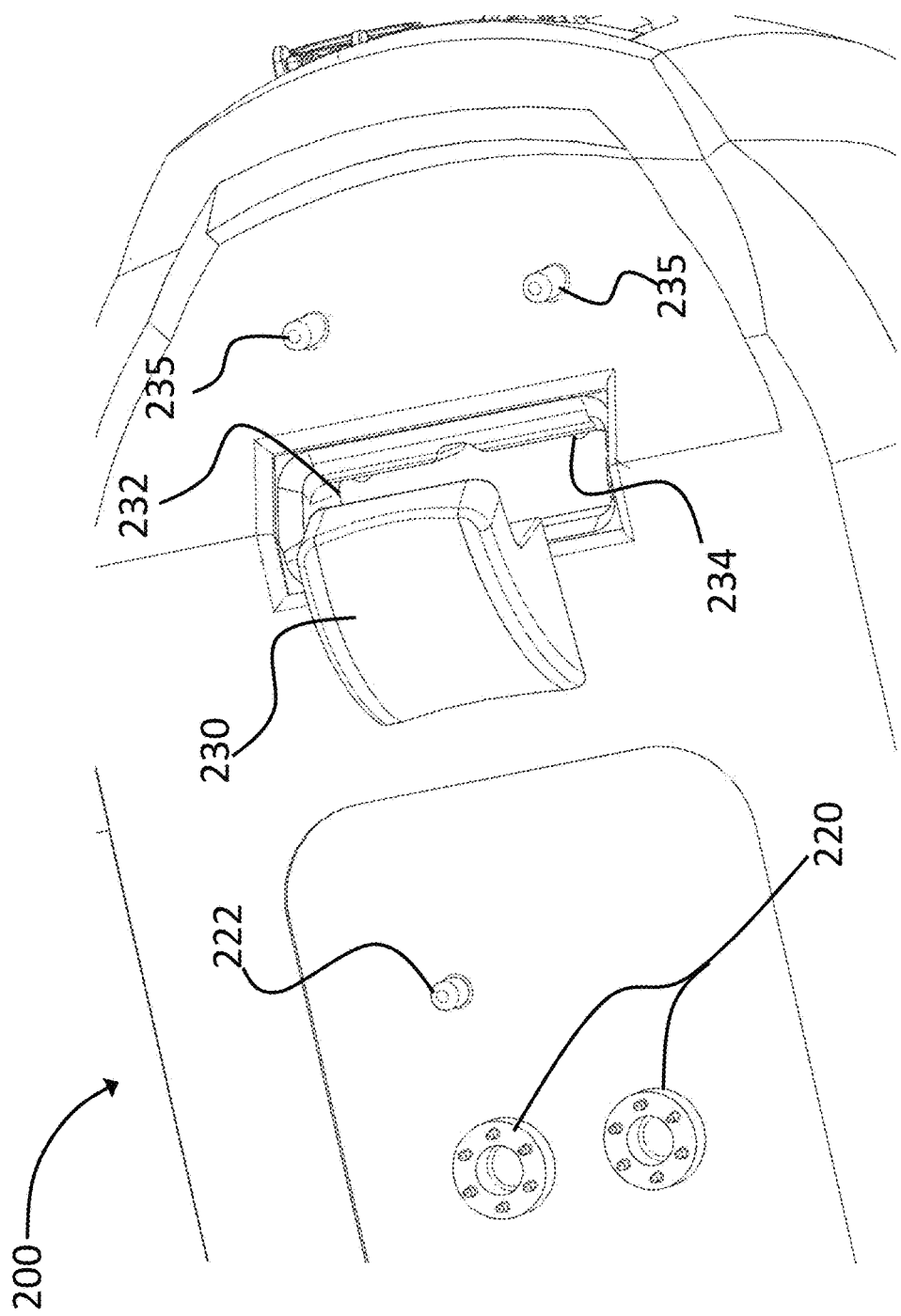
FIG. 7B is an illustrative partial perspective view of the base unit of FIG. 7A.
Figure 8:
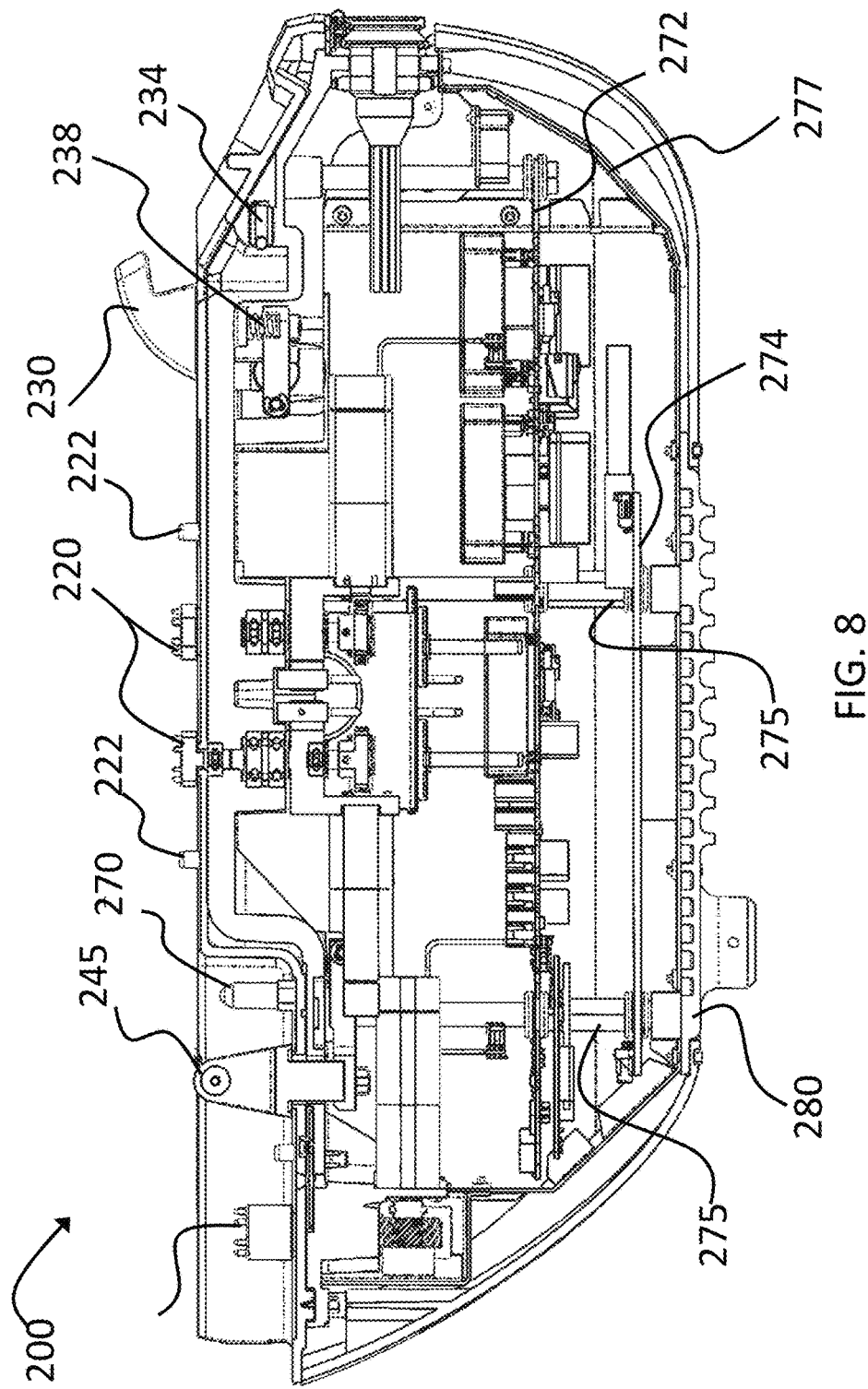
FIG. 8 is an illustrative cross-sectional view of a base unit of a force-transfer driving assembly according to an embodiment of inventive concepts.

FIG. 7A is an illustrative perspective view of a base unit 200 of an articulated robotic probe 175 (shown in FIG. 1A) according to an embodiment of inventive concepts. FIG. 7B is an illustrative partial perspective view of the base unit 200 of FIG. 7A. FIG. 8 is an illustrative cross-sectional view of a base unit 200 of an articulated robotic probe according to an embodiment of inventive concepts. Base unit 200 can be arranged to maximize stability of the robotic probe arm 315 with respect to a patient operating table and serve to permit a feeder assembly 300 to be detachable and replaceable. Base unit 200 comprises a handle, such as a handle 210 configured to allow an operator to carry, engage and/or position base unit 200. A clamping tongue 230 and slot 232 may engage the heel plate 375 of a feeder assembly (components of feeder assembly 300 described with respect to FIGS. 7A, 7B, and 8 have been previously described herein). In an embodiment, clamping tongue 230 is spring loaded with a spring, such as spring 238 of FIG. 8, to exert a clamping force on the top of heel plate 375 during engagement. Slot 232 also includes pressure loaded ball plungers 234 which increase the tightness of fit of heel plate 375 into slot 232, further strengthening and stabilizing the connection between base unit 200 and feeder assembly 300. Base unit 200 includes motor driven wheels 220 which engage and drive bobbins 380. Two motor driven wheels 250 engage and drive gears 340, which in turn drive gears 345 such as to rotate lead screws 320 and advance and retract carriages 325 of force-transfer driving subassembly 320 of the feeder system 300. A bullet pin 270 engages receiving hole 332 of feeder assembly 300. As previously described, this and other projections, including alignment pins 205, 222, and 235, mate with receiving holes, recesses, slots, and/or the surface of feeder assembly 300 to enhance alignment and motion resistance, including yaw between the base unit 200 and feeder assembly 300, and/or any twisting and/or compression of feeder assembly 300. In an embodiment, numerous projections such as described are incorporated into a housing 360, which further stabilizes the interface between base unit 200 and feeder system 300. A mating between alignment pins 395 of the feeder assembly 300 and receiving holes 292 of the base unit 200 further aligns the connection between the male electrical connector 392 and a female connector 290 of the base unit, and also similarly aids in aligning and reinforcing motion resistance between the base unit 200 and feeder assembly 300. In an embodiment, other stabilizing plates, such as plates 274 and 272 of FIG. 8, are incorporated within base unit 200 and are mounted and connected together, such as by vertically oriented support posts 275 of FIG. 8.

In an embodiment, the posts 275 pass through and/or between various stabilizing plates that reinforce their stability with respect to one another and the entire base unit. In an embodiment, a lower stabilizing plate 274 is connected with a base unit mounting plate 280, further described below with respect to FIGS. 9-11. Posts 275 are secured within mounting fixtures 283 of mounting plate 280 to help secure and stabilize the mounting plate with respect to the base unit 200. In an embodiment, posts 275 are constructed of solid metal.

In an embodiment, a faraday cage 277 is mounted to mounting plate 280, and helps block undesired electrical signals from interfering with operation of the robotic system. The faraday cage 277 also provides additional rigidity to the base unit 200 so as to prevent undesired motion caused by robot-generated forces, such as forces exerted on one or more bobbins 380 by a cable attached to bobbin 380 and to a link of inner core 12 or a link of outer sleeve 14 of probe arm 315.

Figure 9:
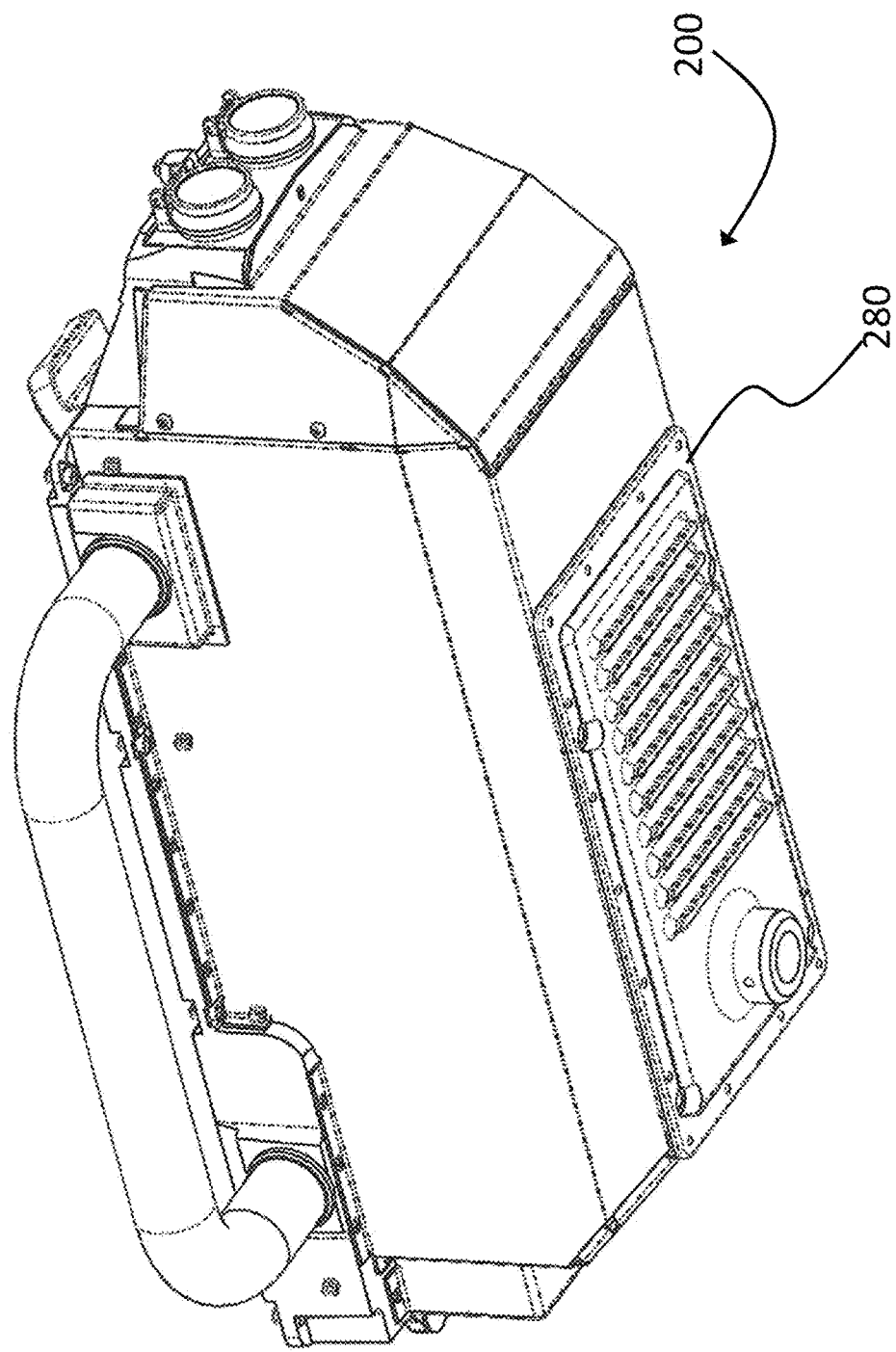
FIG. 9 is a lower perspective view of a base unit of a force-transfer driving assembly according to an embodiment of inventive concepts.
Figure 10:
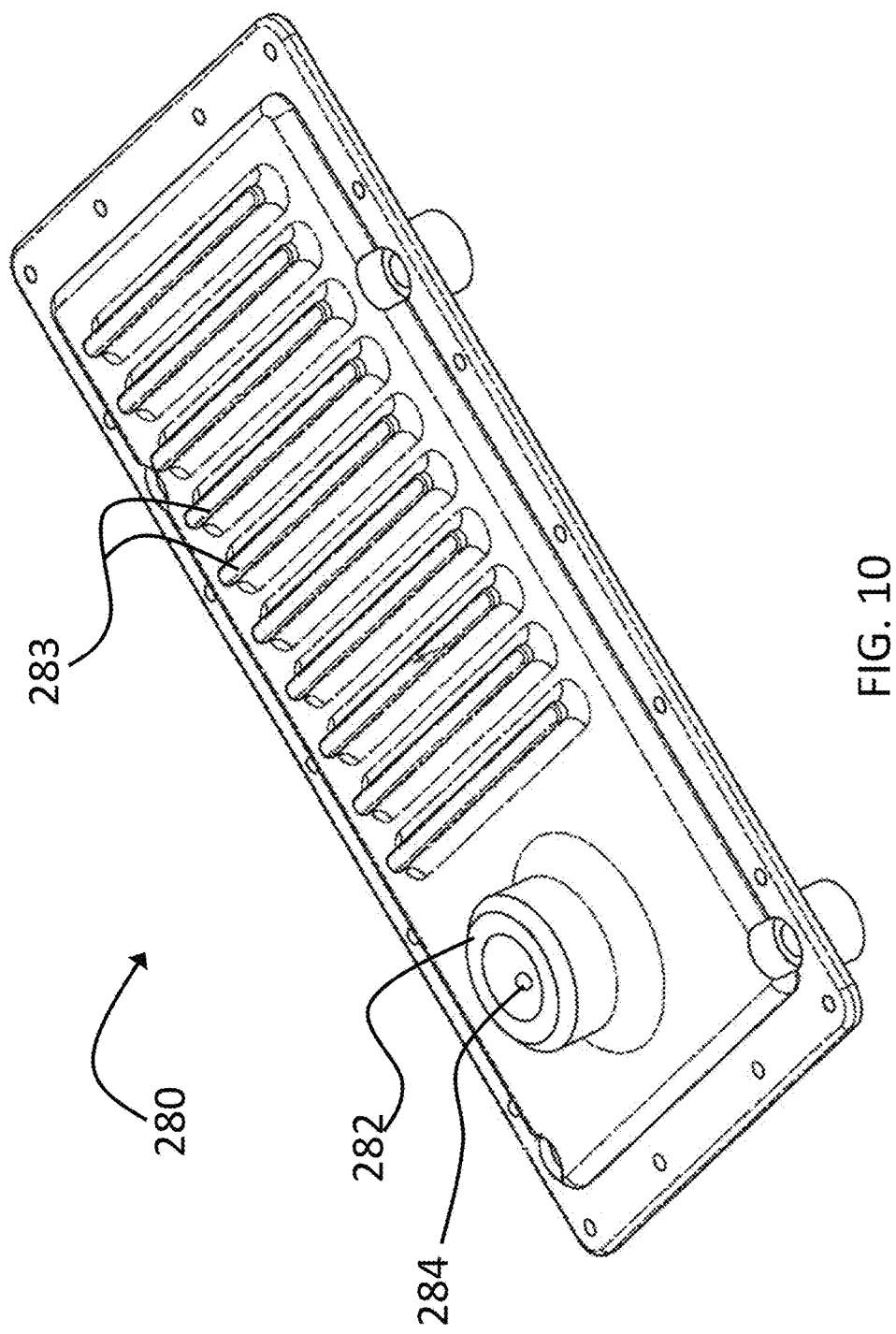
FIG. 10 is an illustrative perspective view of a mounting plate for the base unit of a force-transfer driving assembly according to an embodiment of inventive concepts.

FIG. 9 is a lower perspective view of a base unit 200 of an articulated robotic probe according to an embodiment of inventive concepts, and FIG. 10 is an illustrative perspective view of mounting plate 280 for the base unit 200. Base unit mounting plate 280 includes a stand connecting interface 282 including a locking screw hole 284, which can be used to securely attach base unit 200 to a stand such as, for example, stand 120 of FIG. 1A. In an embodiment, the stand connecting interface can include spacers (e.g., made of plastic), a key hole slotted plastic isolation plate, and insulated standoffs in order to electrically isolate the stand connecting interface from the rest of the base unit. In an embodiment, mounting plate 280 includes heat dissipation elements 283.

As described herein, the systems and methods of the present inventive concepts prevent, mitigate, or otherwise restrict, undesired movement, including bending, torsional rotation, twisting and/or compression of a highly articulated robotic system and its components which support and provide force transfer through the robotic system.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. An apparatus for driving an articulating probe, the apparatus comprising:
   a base structure including a plurality of rotatably driven wheels;
   at least one elongate probe constructed and arranged to articulate in at least one degree of motion and to transition from a flexible state to a rigid state;
   a force transfer mechanism including a plurality of rotatable bobbins coupled to a corresponding plurality of cables in turn coupled to the at least one elongate probe, the force transfer mechanism constructed and arranged to apply a force to the at least one elongate probe, said force selected from the group consisting of:
      a force that causes the at least one elongate probe to articulate in the at least one predetermined degree of motion; and
      a force that causes the at least one elongate probe to transition from the flexible state to the rigid state; and
   a coupling mechanism that removably secures the force transfer mechanism to the base structure to cause the plurality of rotatable bobbins of the force transfer mechanism to interface with the rotatably driven wheels of the base structure so that rotation of the rotatably driven wheels of the base structure causes rotation of the rotatable bobbins, the rotation of the bobbins causing tensioning or de-tensioning of the corresponding cables to apply the force to the at least one elongate probe.

2. The apparatus of claim 1 wherein the at least one elongate probe comprises a first probe arm and a second probe arm, the second probe arm slidable longitudinally within the first probe arm, and
wherein the apparatus further comprises a locking mechanism to selectively rotate the rotatable wheels of the base in turn causing tensioning or de-tensioning of the corresponding cables, to transition each of the first or second probe arms between the flexible state and the rigid state.

3. The apparatus of claim 2 further comprising one or more stabilizing elements constructed and arranged to resist undesired movement of the at least one elongate probe during the selective rotating of the rotatable wheels by the locking mechanism.

4. The apparatus of claim 3 wherein the one or more stabilizing elements comprises a force distribution plate, and wherein the bobbins of the force transfer mechanism are rotatably coupled to the force distribution plate.

5. The apparatus of claim 4 wherein the force transfer mechanism comprises a plastic housing and wherein the force distribution plate comprises a metal plate attached to the plastic housing.

6. The apparatus of claim 2 wherein the force transfer mechanism comprises
a first cart that advances and retracts the first probe arm;
a second cart that advances and retracts the second probe arm, and
first and second gears that interface with corresponding rotary drives of the base that induce advancement and retraction of the first and second probe arms in response to rotation of the corresponding rotary drives of the base in first and second directions of rotation,
wherein the coupling mechanism further causes the first and second gears of the force transfer mechanism to interface with the corresponding rotary drives of the base structure.

7. The apparatus of claim 2 wherein the first probe arm and the second probe arm extend in the longitudinal direction, wherein a link of the first probe arm has an opening having an inner width greater than an outer width of a link of the second probe arm, and wherein the link of the second probe arm extends through, and is movable in a longitudinal direction relative to, the opening of the link of the first probe arm.

8. The apparatus of claim 7 wherein the second probe arm comprises an inner link mechanism of the articulating probe and wherein the first probe arm comprises an outer link mechanism of the articulating probe.

9. The apparatus of claim 7 wherein the at least one elongate probe comprises a steerable distal end and wherein the at least one predetermined degree of motion comprises three degrees of motion about which the steerable distal end can be steered.

10. The apparatus of claim 1 further comprising one or more stabilizing elements constructed and arranged to resist undesired movement of the at least one elongated probe during tensioning or de-tensioning of the corresponding cables.

11. The apparatus of claim 10 wherein at least one of the stabilizing elements is constructed and arranged to resist twisting, flexing, compression, stretching and/or lengthening of the base structure.

12. The apparatus of claim 10 further comprising a housing at least partially covering the force transfer mechanism, wherein at least one of the stabilizing elements comprises a reinforced housing rib connected to the housing.

13. The apparatus of claim 10 wherein the one or more stabilizing elements comprises one or more vertically oriented posts extending between a ground-connecting interface and a chassis of the base structure.

14. The apparatus of claim 10, wherein the one or more stabilizing elements are positioned at the base structure.

15. The apparatus of claim 10, wherein the one or more stabilizing elements are positioned at the force transfer mechanism.

16. The apparatus of claim 10, wherein the one or more stabilizing elements are positioned at the base structure and the force transfer mechanism.

17. The apparatus of claim 1, wherein the cables include a proximal end at least partially wound about the bobbin and a distal end coupled to a distal end of the at least one elongate probe.

18. The apparatus of claim 17, wherein the cables include further include a body portion between the proximal end and the distal end that extends longitudinally through the at least one elongate probe.

19. The apparatus of claim 1 wherein the at least one elongate probe is constructed and arranged to receive a tool.

20. The apparatus of claim 1 wherein the force that causes the at least one elongate probe to transition from the flexible state to the rigid state comprises a force of at least 1 pound.

21. The apparatus of claim 1, wherein the force that causes the at least one elongate probe to transition from the flexible state to the rigid state comprises a force of at least 10 pounds.

22. The apparatus of claim 1, wherein the force that causes the at least one elongate probe to transition from the flexible state to the rigid state comprises a force of at least 20 pounds.

23. The apparatus of claim 1, wherein the force that causes the at least one elongate probe to transition from the flexible state to the rigid state comprises a force of at least 30 pounds.

* * * * *